(12) United States Patent
Shiotsuka et al.

(10) Patent No.: US 7,875,465 B2
(45) Date of Patent: Jan. 25, 2011

(54) TARGET SUBSTANCE CAPTURING MOLECULE

(75) Inventors: Hidenori Shiotsuka, Kawasaki (JP); Satoru Hatakeyama, Kawasaki (JP); Tsuyoshi Nomoto, Tokyo (JP); Masaru Kaieda, Tokyo (JP); Junta Yamamichi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 445 days.

(21) Appl. No.: 11/913,047

(22) PCT Filed: May 29, 2006

(86) PCT No.: PCT/JP2006/311159

§ 371 (c)(1),
(2), (4) Date: Oct. 29, 2007

(87) PCT Pub. No.: WO2006/129828

PCT Pub. Date: Dec. 7, 2006

(65) Prior Publication Data

US 2009/0215197 A1 Aug. 27, 2009

(30) Foreign Application Priority Data

May 31, 2005 (JP) ............................. 2005-160737

(51) Int. Cl.
*G01N 33/566* (2006.01)
(52) U.S. Cl. ....................... 436/501; 436/514; 436/518; 436/547; 436/807; 436/808; 436/810; 530/387.1; 530/387.3; 530/866; 530/867
(58) Field of Classification Search .............. 530/387.1, 530/387.3, 866, 867; 436/514, 518, 547, 436/807, 808, 810, 501
See application file for complete search history.

(56) References Cited

U.S. PATENT DOCUMENTS

| | | | |
|---|---|---|---|
| 5,529,792 A | 6/1996 | Risau et al. | 424/570 |
| 5,653,675 A | 8/1997 | Kanno et al. | 588/249 |
| 5,863,789 A | 1/1999 | Komatsu et al. | 435/262 |
| 5,969,108 A | 10/1999 | McCafferty et al. | 530/387.3 |
| 6,424,418 B2 | 7/2002 | Kawabata et al. | 356/445 |
| 6,472,191 B1 | 10/2002 | Yano et al. | 435/189 |
| 6,686,439 B2 | 2/2004 | Kenmoku et al. | 528/272 |
| 6,803,444 B2 | 10/2004 | Suzuki et al. | 528/361 |
| 6,853,477 B2 | 2/2005 | Nomoto et al. | 359/296 |
| 6,858,417 B2 | 2/2005 | Yano et al. | 435/189 |
| 6,861,496 B2 | 3/2005 | Kenmoku et al. | 528/272 |
| 6,864,074 B2 | 3/2005 | Yano et al. | 435/189 |
| 6,916,861 B2 | 7/2005 | Nomoto et al. | 523/160 |
| 6,951,745 B2 | 10/2005 | Nomoto et al. | 435/118 |
| 7,153,622 B2 | 12/2006 | Honma et al. | 430/105 |
| 7,166,697 B1 * | 1/2007 | Galanis et al. | 530/350 |
| 7,235,396 B2 | 6/2007 | Nomoto et al. | 435/253.3 |
| 2003/0088074 A1 * | 5/2003 | Hamers et al. | 530/387.1 |
| 2003/0144483 A1 | 7/2003 | Tempest et al. | 530/388.22 |
| 2003/0194443 A1 | 10/2003 | Yano et al. | 424/497 |
| 2004/0005638 A1 | 1/2004 | Honma et al. | 435/7.1 |
| 2005/0208635 A1 | 9/2005 | Nomoto et al. | 435/135 |
| 2006/0115861 A1 | 6/2006 | Shiotsuka et al. | 435/7.9 |
| 2006/0172398 A1 | 8/2006 | Nomoto et al. | 435/135 |
| 2006/0172399 A1 | 8/2006 | Nomoto et al. | 435/135 |
| 2006/0275811 A1 | 12/2006 | Hatakeyama et al. | 435/6 |
| 2007/0054315 A1 | 3/2007 | Imamura et al. | 435/7.1 |
| 2007/0131546 A1 | 6/2007 | Nomoto et al. | 204/403.01 |
| 2007/0131547 A1 | 6/2007 | Nomoto et al. | 204/403.01 |
| 2007/0178522 A1 | 8/2007 | Shiotsuka et al. | 435/7.1 |
| 2007/0190590 A1 | 8/2007 | Kubo et al. | 435/25 |

FOREIGN PATENT DOCUMENTS

| | | |
|---|---|---|
| WO | 88/06630 | 9/1988 |
| WO | 92/15606 | 9/1992 |
| WO | 02/20565 | 3/2002 |
| WO | 2004/003019 | 1/2004 |
| WO | 2005/097831 | 10/2005 |

OTHER PUBLICATIONS

Cheong et al., Biochemical and Biophysical Research Communications. vol. 173, No. 3, 1990. pp. 795-800.*
Conrath et al., The Journal of Biological Chemistry. vol. 276, No. 10, Mar. 9, 2001. pp. 7346-7350.*
Miquel A. Andrade, et al., "Comparison of ARM and HEAT Protein Repeats", J. Mol. Biol., vol. 309, 2001, pp. 1-18.
Alisdair B. Boraston, et al., "Carbohydrate-binding modules: fine-tuning polysaccharide recognition", Biochem. J., vol. 382, 2004, pp. 769-781.
Stefan Ewert, et al., "Biophysical Properties of Camelid $V_{HH}$ Domains Compared to Those of Human $V_H3$ Domains", Biochemistry, vol. 41, 2002, pp. 3628-3636.
Akiko Koide, et al., "The Fibronectin Type III Domain as a Scaffold for Novel Binding Proteins", J. Mol. Biol., vol. 284, 1998, pp. 1141-1151.
Dario Neri, et al., "High-affinity Antigen Binding by Chelating Recombinant Antibodies (CRAbs)", J. Mol. Biol., vol. 246, 1995, pp. 367-373.
Karin Nord, et al., "Binding proteins selected from combinatorial libraries of an α-helical bacterial receptor domain", Nature Biotechnology, vol. 15, Aug. 1997, pp. 772-777.
Stewart D. Nuttall, et al., "Isolation of the new antigen receptor from wobbegong sharks, and use as a scaffold for the display of protein loop libraries", Molecular Immunology, vol. 38, 2001, pp. 313-326.

(Continued)

*Primary Examiner*—Bao-Thuy L Nguyen
(74) *Attorney, Agent, or Firm*—Fitzpatrick, Cella, Harper & Scinto

(57) ABSTRACT

A capturing molecule having not less than two domains specifically binding to different sites of a target substance, wherein the not less than two domains comprise (1) a first domain having a hypervariable loop structure at a binding site to the target substance, and (2) a second domain having no hypervariable loop structure at a binding site to the target substance.

12 Claims, 1 Drawing Sheet

OTHER PUBLICATIONS

Erin K. O'Shea, et al., "Mechanism of Specificity in the Fos-Jun Oncoprotein Heterodimer", Cell, vol. 68, Feb. 21, 1992, pp. 699-708.

Erin K. O'Shea, et al., "X-ray Structure of the GCN4 Leucine Zipper, a Two-Stranded, Parallel Coiled Coil", Science, vol. 254, No. 5031, Oct. 25, 1991, pp. 539-544.

Mehmet Sarikaya, et al., "Molecular biomimetics: nanotechnology through biology", Nature Materials, vol. 2, Sep. 2003, pp. 577-585.

Arne Skerra, "'Anticalins': a new class of engineered ligand-binding proteins with antibody-like properties", Reviews in Molecular Biotechnology, vol. 74, 2001, pp. 257-275.

Arne Skerra, "Engineered protein scaffolds for molecular recognition", Journal of Molecular Recognition, vol. 13, 2000, pp. 167-187.

Silvia Spinelli, et al., "Lateral Recognition of a Dye Hapten by a Llama VHH Domain", J. Mol. Biol., vol. 311, 2001, pp. 123-129.

Mårten Andersson, et al., "Inclusion of a non-immunoglobulin binding protein in two-site ELISA for quantification of human serum proteins without interference by heterophilic serum antibodies", Journal of Immunological Methods, vol. 283, 2003, pp. 225-234.

H. Kaspar Binz, et al., "High-affinity binders selected from designed ankyrin repeat protein libraries", Nature Biotechnology, vol. 22, No. 5, May 2004, pp. 575-582.

* cited by examiner

SEQUENCE LISTING

```
<160> NUMBER OF SEQ ID NOS: 24

<210> SEQ ID NO 1
<211> LENGTH: 345
<212> TYPE: DNA
<213> ORGANISM: Artificial sequence
<220> FEATURE:
<223> OTHER INFORMATION: Maltose binding protein-binding VHH

<400> SEQUENCE: 1
caggtgcagc tgcaggaaag cggcccgggc ctgctgaaac cgagcgaaac cctgtttctg      60
acctgcaccg tgagcggctt tagcattagc ggcggctatt attggggctg gtttcgccag     120
ccgccggcga aagaacgcga atggattggc agcgtgtatc atagcggcag cacctattat     180
aataaaagcc tggaaagccg cgtgaccatt agcattcata ccagcgaaag ccagattagc     240
ctgaaactga atagcgtgac cgcggcggat accgcggtgt atagctgcgc gcgctatcgc     300
accgcgcatc cgctgtgggg ccagggcacc atggtgaccg tgagc                    345

<210> SEQ ID NO 2
<211> LENGTH: 116
<212> TYPE: PRT
<213> ORGANISM: Artificial sequence
<220> FEATURE:
<223> OTHER INFORMATION: Maltose binding protein-binding VHH

<400> SEQUENCE: 2

Gln Val Gln Leu Gln Glu Ser Gly Pro Gly Leu Leu Lys Pro Ser Glu
1               5                   10                  15

Thr Leu Phe Leu Thr Cys Thr Val Ser Gly Phe Ser Ile Ser Gly Gly
            20                  25                  30

Tyr Tyr Trp Gly Trp Phe Arg Gln Pro Pro Gly Lys Glu Arg Glu Trp
        35                  40                  45
```

```
Ile Gly Ser Val Tyr His Ser Gly Ser Thr Tyr Tyr Asn Lys Ser Leu
        50                  55                  60

Glu Ser Arg Val Thr Ile Ser Ile His Thr Ser Glu Ser Gln Ile Ser
65                  70                  75                  80

Leu Lys Leu Asn Ser Val Thr Ala Ala Asp Thr Ala Val Tyr Ser Cys
                85                  90                  95

Ala Arg Tyr Arg Thr Ala His Pro Leu Trp Gly Gln Gly Thr Met Val
                100                 105                 110

Thr Val Ser Ser
        115

<210> SEQ ID NO 3
<211> LENGTH: 362
<212> TYPE: DNA
<213> ORGANISM: Artificial sequence
<220> FEATURE:
<223> OTHER INFORMATION: Maltose binding protein-binding VHH
<220> FEATURE:
<221> NAME/KEY: misc_feature
<222> LOCATION: (1)..(5)
<223> OTHER INFORMATION: n is a, c, g, or t

<400> SEQUENCE: 3
nnnnnccatg gcaggtgcag ctgcaggaaa gcggcccggg cctgctgaaa ccgagcgaaa      60
ccctgttcct gacctgcacc gtgagcggct ttagcattag cggcggctat tattggggct    120
ggtttcgcca gccgccggcg aaagaacgcg aatggattgg cagcgtgtat catagcggca    180
gcacctatta taataaaagc ctggaaagcc gcgtgaccat tagcattcat accagcgaaa    240
gccagattag cctgaaactg aatagcgtga ccgcggcgga taccgcggtg tatagctgcg    300
cgcgctatcg caccgcgcat ccgctgtggg gccagggcac catggtgacc gtgagcgaat    360
tc                                                                    362

<210> SEQ ID NO 4
<211> LENGTH: 120
<212> TYPE: PRT
<213> ORGANISM: Artificial sequence
<220> FEATURE:
<223> OTHER INFORMATION: Maltose binding protein-binding VHH

<400> SEQUENCE: 4

Pro Trp Gln Val Gln Leu Gln Glu Ser Gly Pro Gly Leu Leu Lys Pro
1               5                   10                  15

Ser Glu Thr Leu Phe Leu Thr Cys Thr Val Ser Gly Phe Ser Ile Ser
                20                  25                  30

Gly Gly Tyr Tyr Trp Gly Trp Phe Arg Gln Pro Pro Gly Lys Glu Arg
            35                  40                  45

Glu Trp Ile Gly Ser Val Tyr His Ser Gly Ser Thr Tyr Tyr Asn Lys
        50                  55                  60

Ser Leu Glu Ser Arg Val Thr Ile Ser Ile His Thr Ser Glu Ser Gln
65                  70                  75                  80

Ile Ser Leu Lys Leu Asn Ser Val Thr Ala Ala Asp Thr Ala Val Tyr
                85                  90                  95

Ser Cys Ala Arg Tyr Arg Thr Ala His Pro Leu Trp Gly Gln Gly Thr
                100                 105                 110

Met Val Thr Val Ser Ser Glu Phe
        115                 120
```

<210> SEQ ID NO 5
<211> LENGTH: 378
<212> TYPE: DNA
<213> ORGANISM: Artificial sequence
<220> FEATURE:
<223> OTHER INFORMATION: Maltose binding protein-binding ankyrine

<400> SEQUENCE: 5

```
aatgctgctg acaatactgg tactactccg ctgcacctgg ctgcttattc tggtcacctg      60
gaaatcgttg aagttctgct gaagcacggt gctgacgttg acgcttctga cgttttggt     120 tatactccgc tgcacctggc tgcttattgg ggtcacctgg aaatcgttga agttctgctg    180
aagaacggtg ctgacgttaa cgctatggac tctgatggta tgactccact gcacctggct    240
gctaagtggg gttacctgga aatcgttgaa gttctgctga agcacggtgc tgacgttaac    300
gctcaggaca aattcggtaa gaccgctttc gacatctcca tcgacaacgg taacgaggac    360
ctggctgaaa tcctgcaa                                                   378
```

<210> SEQ ID NO 6
<211> LENGTH: 126
<212> TYPE: PRT
<213> ORGANISM: Artificial Sequence
<220> FEATURE:
<223> OTHER INFORMATION: Maltose binding protein-binding ankyrine

<400> SEQUENCE: 6

```
Asn Ala Ala Asp Asn Thr Gly Thr Thr Pro Leu His Leu Ala Ala Tyr
1               5                  10                  15

Ser Gly His Leu Glu Ile Val Glu Val Leu Leu Lys His Gly Ala Asp
            20                  25                  30

Val Asp Ala Ser Asp Val Phe Gly Tyr Thr Pro Leu His Leu Ala Ala
        35                  40                  45

Tyr Trp Gly His Leu Glu Ile Val Glu Val Leu Leu Lys Asn Gly Ala
    50                  55                  60

Asp Val Asn Ala Met Asp Ser Asp Gly Met Thr Pro Leu His Leu Ala
65                  70                  75                  80

Ala Lys Trp Gly Tyr Leu Glu Ile Val Glu Val Leu Leu Lys His Gly
                85                  90                  95

Ala Asp Val Asn Ala Gln Asp Lys Phe Gly Lys Thr Ala Phe Asp Ile
            100                 105                 110

Ser Ile Asp Asn Gly Asn Glu Asp Leu Ala Glu Ile Leu Gln
        115                 120                 125
```

<210> SEQ ID NO 7
<211> LENGTH: 443
<212> TYPE: DNA
<213> ORGANISM: Artificial sequence
<220> FEATURE:
<223> OTHER INFORMATION: G3ANK coding DNA
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (440)..(443)
<223> OTHER INFORMATION: n is a, c, g, or t

<400> SEQUENCE: 7

```
nnnngaatcc ggcggggggcg gtagcggcgg tggcgggtcg ggcggtggcg gatcgaatgc     60
tgctgacaat actggtacta ctccgctgca cctggctgct tattctggtc acctggaaat    120
```

-continued

```
cgttgaagtt ctgctgaagc acggtgctga cgttgacgct tctgacgttt ttggttatac      180
tccgctgcac ctggctgctt attggggtca cctggaaatc gttgaagttc tgctgaagaa      240
cggtgctgac gttaacgcta tggactctga tggtatgact ccactgcacc tggctgctaa      300
gtggggttac ctggaaatcg ttgaagttct gctgaagcac ggtgctgacg ttaacgctca      360
ggacaaattc ggtaagaccg ctttcgacat ctccatcgac aacggtaacg aggacctggc      420
tgaaatcctg caaaggcttn nnn                                              443
```

<210> SEQ ID NO 8
<211> LENGTH: 145
<212> TYPE: PRT
<213> ORGANISM: Artificial sequence
<220> FEATURE:
<223> OTHER INFORMATION: G3-ankyrine

<400> SEQUENCE: 8

```
Glu Phe Gly Gly Gly Gly Ser Gly Gly Gly Gly Ser Gly Gly Gly Gly
1               5                   10                  15

Ser Asn Ala Ala Asp Asn Thr Gly Thr Thr Pro Leu His Leu Ala Ala
            20                  25                  30

Tyr Ser Gly His Leu Glu Ile Val Glu Val Leu Leu Lys His Gly Ala
        35                  40                  45

Asp Val Asp Ala Ser Asp Val Phe Gly Tyr Thr Pro Leu His Leu Ala
    50                  55                  60

Ala Tyr Trp Gly His Leu Glu Ile Val Glu Val Leu Leu Lys Asn Gly
65                  70                  75                  80

Ala Asp Val Asn Ala Met Asp Ser Asp Gly Met Thr Pro Leu His Leu
                85                  90                  95

Ala Ala Lys Trp Gly Tyr Leu Glu Ile Val Glu Val Leu Leu Lys His
            100                 105                 110

Gly Ala Asp Val Asn Ala Gln Asp Lys Phe Gly Lys Thr Ala Phe Asp
        115                 120                 125

Ile Ser Ile Asp Asn Gly Asn Glu Asp Leu Ala Glu Ile Leu Gln Arg
    130                 135                 140

Leu
145
```

<210> SEQ ID NO 9
<211> LENGTH: 443
<212> TYPE: DNA
<213> ORGANISM: Artificial sequence
<220> FEATURE:
<223> OTHER INFORMATION: G3ANK coding DNA
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (440)..(443)
<223> OTHER INFORMATION: n is a, c, g, or t

<400> SEQUENCE: 9

```
nnnnccatcc ggcgggggcg gtagcggcgg tggcgggtcg ggcggtggcg gatcgaatgc      60
tgctgacaat actggtacta ctccgctgca cctggctgct tattctggtc acctggaaat     120
cgttgaagtt ctgctgaagc acggtgctga cgttgacgct tctgacgttt ttggttatac     180
tccgctgcac ctggctgctt attggggtca cctggaaatc gttgaagttc tgctgaagaa     240
cggtgctgac gttaacgcta tggactctga tggtatgact ccactgcacc tggctgctaa     300
```

```
gtggggttac ctggaaatcg ttgaagttct gctgaagcac ggtgctgacg ttaacgctca      360
ggacaaattc ggtaagaccg ctttcgacat ctccatcgac aacggtaacg aggacctggc      420
tgaaatcctg caaaggcttn nnn                                              443
```

<210> SEQ ID NO 10
<211> LENGTH: 130
<212> TYPE: PRT
<213> ORGANISM: Artificial sequence
<220> FEATURE:
<223> OTHER INFORMATION: G3-ankyrine

<400> SEQUENCE: 10

```
Pro Leu Asn Ala Ala Asp Asn Thr Gly Thr Thr Pro Leu His Leu Ala
1               5                   10                  15

Ala Tyr Ser Gly His Leu Glu Ile Val Glu Val Leu Leu Lys His Gly
            20                  25                  30

Ala Asp Val Asp Ala Ser Asp Val Phe Gly Tyr Thr Pro Leu His Leu
        35                  40                  45

Ala Ala Tyr Trp Gly His Leu Glu Ile Val Glu Val Leu Leu Lys Asn
    50                  55                  60

Gly Ala Asp Val Asn Ala Met Asp Ser Asp Gly Met Thr Pro Leu His
65                  70                  75                  80

Leu Ala Ala Lys Trp Gly Tyr Leu Glu Ile Val Glu Val Leu Leu Lys
                85                  90                  95

His Gly Ala Asp Val Asn Ala Gln Asp Lys Phe Gly Lys Thr Ala Phe
            100                 105                 110

Asp Ile Ser Ile Asp Asn Gly Asn Glu Asp Leu Ala Glu Ile Leu Gln
        115                 120                 125

Arg Leu
    130
```

<210> SEQ ID NO 11
<211> LENGTH: 184
<212> TYPE: DNA
<213> ORGANISM: Artificial sequence
<220> FEATURE:
<223> OTHER INFORMATION: G3-jun coding DNA
<220> FEATURE:
<221> NAME/KEY: misc_feature
<222> LOCATION: (1)..(4)
<223> OTHER INFORMATION: n is a, c, g, or t

<400> SEQUENCE: 11

```
nnnngaatcc ggcgggggcg gtagcggcgg tggcgggtcg ggcggtggcg gatcgcgtat      60
cgctcgtctc gaggaaaaag ttaaaaccct gaaagctcag aactccgaac tggcttccac     120
cgctaacatg ctgcgtgaac aggttgctca gctgaaacag aaagttatga actacaggct     180
ttgc                                                                  184
```

<210> SEQ ID NO 12
<211> LENGTH: 60
<212> TYPE: PRT
<213> ORGANISM: Artificial sequence
<220> FEATURE:
<223> OTHER INFORMATION: G3-Jun

<400> SEQUENCE: 12

```
Glu Phe Gly Gly Gly Gly Ser Gly Gly Gly Gly Ser Gly Gly Gly Gly
1               5                   10                  15
```

Ser Arg Ile Ala Arg Leu Glu Glu Lys Val Lys Thr Leu Lys Ala Gln
            20                  25                  30

Asn Ser Glu Leu Ala Ser Thr Ala Asn Met Leu Arg Glu Gln Val Ala
        35                  40                  45

Gln Leu Lys Gln Lys Val Met Asn Tyr Arg Leu Cys
    50                  55                  60

<210> SEQ ID NO 13
<211> LENGTH: 184
<212> TYPE: DNA
<213> ORGANISM: Artificial sequence
<220> FEATURE:
<223> OTHER INFORMATION: G3-Fos coding DNA
<220> FEATURE:
<221> NAME/KEY: misc_feature
<222> LOCATION: (1)..(4)
<223> OTHER INFORMATION: n is a, c, g, or t

<400> SEQUENCE: 13
nnnngaatcc ggcgggggcg gtagcggcgg tggcgggtcg ggcggtggcg gatcgctgac      60
cgacaccctg caggctgaaa ccgaccagct ggaagacaaa aaatccgctc tgcagaccga     120
aatcgctaac ctgctgaaag aaaaagaaaa actggaattt atcctggctg cttacaggct     180
ttgc                                                                  184

<210> SEQ ID NO 14
<211> LENGTH: 60
<212> TYPE: PRT
<213> ORGANISM: Artificial sequence
<220> FEATURE:
<223> OTHER INFORMATION: G3-Fos

<400> SEQUENCE: 14

Glu Phe Gly Gly Gly Gly Ser Gly Gly Gly Gly Ser Gly Gly Gly Gly
1               5                   10                  15

Ser Leu Thr Asp Thr Leu Gln Ala Glu Thr Asp Gln Leu Glu Asp Lys
            20                  25                  30

Lys Ser Ala Leu Gln Thr Glu Ile Ala Asn Leu Leu Lys Glu Lys Glu
        35                  40                  45

Lys Leu Glu Phe Ile Leu Ala Ala Tyr Arg Leu Cys
    50                  55                  60

<210> SEQ ID NO 15
<211> LENGTH: 786
<212> TYPE: DNA
<213> ORGANISM: Artificial sequence
<220> FEATURE:
<223> OTHER INFORMATION: scVA coding DNA

<400> SEQUENCE: 15
ccatggcagg tgcagctgca ggaaagcggc ccgggcctgc tgaaaccgag cgaaaccctg      60
tttctgacct gcaccgtgag cggctttagc attagcggcg gctattattg gggctggttt     120
cgccagcccg ccggcgaaag acgcgaatgg attggcagcg tgtatcatag cggcagcacc     180
tattataata aaagcctgga aagccgcgtg accattagca ttcataccag cgaaagccag     240
attagcctga aactgaatag cgtgaccgcg gcggataccg cggtgtatag ctgcgcgcgc     300
tatcgcaccg cgcatccgct gtggggccag ggcaccatgg tgaccgtgag cgaattcggc     360
gggggcggta gcggcggtgg cgggtcgggc ggtggcggat cgaatgctgc tgacaatact     420
ggtactactc cgctgcacct ggctgcttat tctggtcacc tggaaatcgt tgaagttctg     480

```
ctgaagcacg gtgctgacgt tgacgcttct gacgttttg gttatactcc gctgcacctg    540
gctgcttatt ggggtcacct ggaaatcgtt gaagttctgc tgaagaacgg tgctgacgtt    600
aacgctatgg actctgatgg tatgactcca ctgcacctgg ctgctaagtg gggttacctg    660
gaaatcgttg aagttctgct gaagcacggt gctgacgtta acgctcagga caaattcggt    720
aagaccgctt tcgacatctc catcgacaac ggtaacgagg acctggctga atcctgcaa    780 aggctt                                                                786
```

<210> SEQ ID NO 16
<211> LENGTH: 263
<212> TYPE: PRT
<213> ORGANISM: Artificial sequence
<220> FEATURE:
<223> OTHER INFORMATION: scVA

<400> SEQUENCE: 16

```
Pro Trp Gln Val Gln Leu Gln Glu Ser Gly Pro Gly Leu Leu Lys Pro
1               5                   10                  15

Ser Glu Thr Leu Phe Leu Thr Cys Thr Val Ser Gly Phe Ser Ile Ser
            20                  25                  30

Gly Gly Tyr Tyr Trp Gly Trp Phe Arg Gln Pro Pro Gly Lys Glu Arg
        35                  40                  45

Glu Trp Ile Gly Ser Val Tyr His Ser Gly Ser Thr Tyr Tyr Asn Lys
    50                  55                  60

Ser Leu Glu Ser Arg Val Thr Ile Ser Ile His Thr Ser Glu Ser Gln
65                  70                  75                  80

Ile Ser Leu Lys Leu Asn Ser Val Thr Ala Ala Asp Thr Ala Val Tyr
                85                  90                  95

Ser Cys Ala Arg Tyr Arg Thr Ala His Pro Leu Trp Gly Gln Gly Thr
            100                 105                 110

Met Val Thr Val Ser Ser Glu Phe Gly Gly Gly Ser Gly Gly Gly
        115                 120                 125

Gly Ser Gly Gly Gly Gly Ser Asn Ala Ala Asp Asn Thr Gly Thr Thr
    130                 135                 140

Pro Leu His Leu Ala Ala Tyr Ser Gly His Leu Glu Ile Val Glu Val
145                 150                 155                 160

Leu Leu Lys His Gly Ala Asp Val Asp Ala Ser Asp Val Phe Gly Tyr
                165                 170                 175

Thr Pro Leu His Leu Ala Ala Tyr Trp Gly His Leu Glu Ile Val Glu
            180                 185                 190

Val Leu Leu Lys Asn Gly Ala Asp Val Asn Ala Met Asp Ser Asp Gly
        195                 200                 205

Met Thr Pro Leu His Leu Ala Ala Lys Trp Gly Tyr Leu Glu Ile Val
    210                 215                 220

Glu Val Leu Leu Lys His Gly Ala Asp Val Asn Ala Gln Asp Lys Phe
225                 230                 235                 240

Gly Lys Thr Ala Phe Asp Ile Ser Ile Asp Asn Gly Asn Glu Asp Leu
                245                 250                 255

Ala Glu Ile Leu Gln Arg Leu
            260
```

<210> SEQ ID NO 17
<211> LENGTH: 531
<212> TYPE: DNA
<213> ORGANISM: Artificial sequence
<220> FEATURE:

<223> OTHER INFORMATION: MBP binding VHH-Jun coding DNA

<400> SEQUENCE: 17

```
ccatggcagg tgcagctgca ggaaagcggc ccgggcctgc tgaaaccgag cgaaaccctg      60
tttctgacct gcaccgtgag cggctttagc attagcggcg gctattattg gggctggttt     120
cgccagccgc cggcgaaaga acgcgaatgg attggcagcg tgtatcatag cggcagcacc     180
tattataata aaagcctgga aagccgcgtg accattagca ttcataccag cgaaagccag     240
attagcctga aactgaatag cgtgaccgcg gcggataccg cggtgtatag ctgcgcgcgc     300
tatcgcaccg cgcatccgct gtggggccag ggcaccatgg tgaccgtgag cgaattcggc     360
ggggcggta gcggcggtgg cgggtcgggc ggtggcggat cgcgtatcgc tcgtctcgag      420
gaaaaagtta aaaccctgaa agctcagaac tccgaactgg cttccaccgc taacatgctg     480
cgtgaacagg ttgctcagct gaaacagaaa gttatgaact acttcggatg c              531
```

<210> SEQ ID NO 18
<211> LENGTH: 178
<212> TYPE: PRT
<213> ORGANISM: Artificial sequence
<220> FEATURE:
<223> OTHER INFORMATION: MBP binding VHH-Jun

<400> SEQUENCE: 18

```
Pro Trp Gln Val Gln Leu Gln Glu Ser Gly Pro Gly Leu Leu Lys Pro
1               5                   10                  15

Ser Glu Thr Leu Phe Leu Thr Cys Thr Val Ser Gly Phe Ser Ile Ser
            20                  25                  30

Gly Gly Tyr Tyr Trp Gly Trp Phe Arg Gln Pro Pro Gly Lys Glu Arg
        35                  40                  45

Glu Trp Ile Gly Ser Val Tyr His Ser Gly Ser Thr Tyr Tyr Asn Lys
    50                  55                  60

Ser Leu Glu Ser Arg Val Thr Ile Ser Ile His Thr Ser Glu Ser Gln
65                  70                  75                  80

Ile Ser Leu Lys Leu Asn Ser Val Thr Ala Ala Asp Thr Ala Val Tyr
                85                  90                  95

Ser Cys Ala Arg Tyr Arg Thr Ala His Pro Leu Trp Gly Gln Gly Thr
            100                 105                 110

Met Val Thr Val Ser Ser Glu Phe Gly Gly Gly Ser Gly Gly Gly
        115                 120                 125

Gly Ser Gly Gly Gly Ser Arg Ile Ala Arg Leu Glu Glu Lys Val
    130                 135                 140

Lys Thr Leu Lys Ala Gln Asn Ser Glu Leu Ala Ser Thr Ala Asn Met
145                 150                 155                 160

Leu Arg Glu Gln Val Ala Gln Leu Lys Gln Lys Val Met Asn Tyr Phe
                165                 170                 175

Gly Cys
```

<210> SEQ ID NO 19
<211> LENGTH: 558
<212> TYPE: DNA
<213> ORGANISM: Artificial sequence
<220> FEATURE:
<223> OTHER INFORMATION: MBP binding ankyrineFos coding DNA

<400> SEQUENCE: 19

```
aatgctgctg acaatactgg tactactccg ctgcacctgg ctgcttattc tggtcacctg      60
```

-continued

```
gaaatcgttg aagttctgct gaagcacggt gctgacgttg acgcttctga cgttttggt     120 tatactccgc tgcacctggc tgcttattgg ggtcacctgg aaatcgttga agttctgctg    180
aagaacggtg ctgacgttaa cgctatggac tctgatggta tgactccact gcacctggct    240
gctaagtggg gttacctgga aatcgttgaa gttctgctga agcacggtgc tgacgttaac    300
gctcaggaca aattcggtaa gaccgctttc gacatctcca tcgacaacgg taacgaggac    360
ctggctgaaa tcctgcaaga atccggcggg ggcgtagcg cgcgtggcgg gtcgggcggt     420
ggcggatcgc tgaccgacac cctgcaggct gaaaccgacc agctggaaga caaaaaatcc    480
gctctgcaga ccgaaatcgc taacctgctg aagaaaaag aaaaactgga atttatcctg     540
gctgcttact tcggatgc                                                  558
```

<210> SEQ ID NO 20
<211> LENGTH: 166
<212> TYPE: PRT
<213> ORGANISM: Artificial sequence
<220> FEATURE:
<223> OTHER INFORMATION: MBP binding ankyrineFos

<400> SEQUENCE: 20

```
Pro Trp Asn Ala Ala Asp Asn Thr Gly Thr Thr Pro Leu His Leu Ala
1               5                   10                  15

Ala Tyr Ser Gly His Leu Glu Ile Val Glu Val Leu Leu Lys His Gly
            20                  25                  30

Ala Asp Val Asp Ala Ser Asp Val Phe Gly Tyr Thr Pro Leu His Leu
        35                  40                  45

Ala Ala Tyr Trp Gly His Leu Glu Ile Val Glu Val Leu Leu Lys Asn
    50                  55                  60

Gly Ala Asp Val Asn Ala Met Asp Ser Asp Gly Met Thr Pro Leu His
65                  70                  75                  80

Leu Ala Ala Lys Trp Gly Tyr Leu Glu Ile Val Glu Val Leu Leu Lys
                85                  90                  95

His Gly Ala Asp Val Asn Ala Gln Asp Lys Phe Gly Lys Thr Ala Phe
            100                 105                 110

Asp Ile Ser Ile Asp Asn Gly Asn Glu Asp Leu Ala Glu Ile Leu Gln
        115                 120                 125

Glu Phe Gly Gly Gly Gly Ser Gly Gly Gly Ser Gly Gly Gly
    130                 135                 140

Ser Leu Thr Asp Thr Leu Gln Ala Glu Thr Asp Gln Leu Glu Asp Lys
145                 150                 155                 160

Lys Ser Ala Leu Gln Cys
                165
```

<210> SEQ ID NO 21
<211> LENGTH: 31
<212> TYPE: DNA
<213> ORGANISM: Artificial sequence
<220> FEATURE:
<223> OTHER INFORMATION: AF-fw
<220> FEATURE:
<221> NAME/KEY: misc_feature
<222> LOCATION: (1)..(4)
<223> OTHER INFORMATION: n is a, c, g, or t

<400> SEQUENCE: 21

```
nnnngcatgc aaattaatac gactcactat a                                    31
```

<210> SEQ ID NO 22

```
<211> LENGTH: 33
<212> TYPE: DNA
<213> ORGANISM: Artificial sequence
<220> FEATURE:
<223> OTHER INFORMATION: AF-fw
<220> FEATURE:
<221> NAME/KEY: misc_feature
<222> LOCATION: (1)..(4)
<223> OTHER INFORMATION: n is a, c, g, or t

<400> SEQUENCE: 22
nnnnagatct caaaaaaccc ctcaagaccc gtt                               33

<210> SEQ ID NO 23
<211> LENGTH: 36
<212> TYPE: DNA
<213> ORGANISM: Artificial sequence
<220> FEATURE:
<223> OTHER INFORMATION: Maltose binding protein-binding peptide coding
      DNA

<400> SEQUENCE: 23
attccgattc atcgccgtcg cgaatttaat accggc                            36

<210> SEQ ID NO 24
<211> LENGTH: 12
<212> TYPE: PRT
<213> ORGANISM: Artificial sequence
<220> FEATURE:
<223> OTHER INFORMATION: Maltose binding protein-binding peptide

<400> SEQUENCE: 24

Thr Pro Ile His Arg Arg Arg Gln Phe Asn Thr Gly
1               5                   10
```

TARGET SUBSTANCE CAPTURING MOLECULE

TECHNICAL FIELD

The present invention relates to a target substance capturing molecule which is useful for isolating and detecting the target substance, a method of detecting the target substance and a kit for use in the method.

BACKGROUND ART

A bio-molecule specifically binding to a target substance or a low molecular compound targeting a biomolecule is expected as a medicinal drug candidate, which binds specifically to a target substance, thereby producing a useful physiological activity in a living body. Such a bio-molecule or a low molecular compound is also expected as a target-substance capturing molecule of a biosensor by using the specific binding ability thereof to the aforementioned target substance.

As an example of such a bio-molecule, an antibody may be mentioned. The antibody specifically binds to various types of foreign substances invading into the body fluid of an animal by recognizing various structures on the surfaces of the foreign substances and detoxicates them by the immune system. In short, the antibody is one of the proteins functioning in a self-defense mechanism. To function such a mechanism effectively, the antibody has a molecular diversity (that is, having a number of different amino acid sequences in order to bind to various foreign substances). The number of kinds of antibodies is estimated $10^7$ to $10^8$ per animal individual. Since an antibody has such specific antigen recognition ability, high antigen binding ability and molecular diversity, it is expected as a medicinal drug candidate and a target-substance capturing molecule.

The antibody is a protein generally 150 kDa consisting of two of two types of polypeptide chains; one is called a heavy chain of about 50 kDa, and the other is called a light chain of about 25 kDa.

The heavy chain and the light chain each have a variable region and a constant region. The light chain is a polypeptide chain constituted of two domains; one is a variable region (called a light chain variable region: VL) and the other is a constant region (CL). On the other hand, the heavy chain is a polypeptide chain constituted of 4 domains, that is, a single variable region (heavy chain variable region: VH) and three constant regions (CH1 to CH3). Each domain consists of about 110 amino acids and has a cylindrical structure, in which β-sheets are arranged in antiparallel and mutually connected via an S—S bond to form a very stable layer structure.

Antibody molecules characteristically have the binding diversification capable of binding to various types of antigens. The binding diversification is ascribed to the diversity in amino acid sequences of three complementarity determining regions (CDRs) having a loop structure and present in each of the variable regions (VH and VL). The CDR is also called a hypervariable region. Each domain of the VH and VL has three CDRs. These CDRs are arranged on the surface of an antibody molecule and separated from each other by a region called a framework, which has a relatively common amino acid sequences between the VH and VL domains. The antibody recognizes a spatial arrangement of functional groups of a recognition site (antigenic determinant: epitope) of an object, a target substance by its CDR's configuration. By virtue of this, the antibody can recognize a molecule very specifically.

Antibodies can be produced by a method in which a desired antigenic substance is injected in combination with an adjuvant to an animal recipient (such as a rabbit, goat or mouse) at predetermined time intervals and antibodies present in the serum are recovered. Antibodies can be also produced by another method in which B cells capable of producing the antibodies are taken from the aforementioned animal recipient, fused with established tumor cells to prepare hybridoma cells, and then, the hybridoma cells are allowed to produce antibodies, followed by purifying the antibodies.

The antibodies produced by the former method contain various types of antibodies (a mixture of antibodies) recognizing different structures on the surface of the antigenic substance used in immunization. Such a serum containing a plurality of antibodies binding to a single antigen is called a polyclonal antibody. The antibodies produced by the latter method are called a monoclonal antibody. This is because since the antibody-producing B cells can produce only one type of antibody. The antibodies produced from one of the hybridoma cells mentioned above come to be single-type monoclonal antibodies.

In either method, an animal must be immunized with a target substance, an antigen. Whether an antibody, that is, a capturing molecule binding to a desired target substance, is obtained or not cannot be confirmed until the antibodies or the serum is taken and its titer (avidity) is checked. In short, in either a polyclonal antibody or a monoclonal antibody, the characteristics of the antibody obtained vary depending upon the immune system of an animal to be immunized. Furthermore, even if the hybridoma cells capable of producing a monoclonal antibody exhibiting a binding ability to a target substance can be obtained, an efficient genetic engineering method has not yet been found for improving the binding ability of the obtained antibody, at present. Moreover, generally, production of an antibody against a target substance having an analogous structure to that of a bio-constituent of an animal recipient, such as a sugar and a lipid, cannot be expected even if it is a non-self substance. In other words, production of an antibody specifically binding to such a target substance cannot be expected in the immune system serving as a bio-defense system.

On the other hand, a combinatorial method is disclosed to obtain a capturing molecule binding to a target substance by using, for example, an antibody fragment containing at least a part of VH and VL, serving as a binding portion (such as Fab and a single chain Fv (scFv)) of an antibody to an antigen. In U.S. Pat. No. 5,969,108, there is a known technique that an antibody fragment as described above is fused with a phage, in particular, a coating protein of a fibrous phage, and used as a phage antibody having an antibody exposed on the surface. Such a phage having an antibody exposed on the surface of the coating protein is disclosed in not only U.S. Pat. No. 5,969,108 but also the pamphlet of International Publication WO88/06630, WO92/15606, those disclose that the phage is used in a method of selecting a clone of an antibody fragment. According to these methods, a clone capable of binding a target substance can be easily obtained compared to a conventional immunization method for obtaining an antibody. In short, a conventional method for producing antibodies, which is said to be difficult to express other than in animal cells, can be improved by cleaving an antibody into fragments to lower the molecule weight.

In an antibody exposure method represented by the aforementioned method, first, a leading antibody fragment binding to a target substance is obtained under a specific selection pressure and mutated by a genetic engineering approach. Then, a binding/selection experiment is repeatedly performed. As a result, an antibody fragment having a higher binding ability to the target substance can be obtained. These antibody exposure methods have a characteristic feature in that since the complicated immune system of a living body is not used to obtain an antibody to be bound to a target substance, it does not a matter whether an antigen is self-derived or nonself-derived. Furthermore, if a gene portion encoding the CDR portion of an antibody fragment is chemically synthesized, the size of a gene library also can be enlarged.

J. Mol. Biol., 1995, 246, 367-373 discloses improving the binding ability to a target substance HEL. To be more specifically, the document discloses that scFv (derived from D1.3 and HyHEL10) capable of binding to HEL is genetically fused to obtain a single stranded scFv dimer, which shows improved binding ability to HEL. Similarly, International Publication WO2004/003019 pamphlet also suggests a technology regarding a target substance-capturing molecule that recognizes two different epitopes present on the surface of the same single target substance molecule although unfortunately, it fails to mention specific techniques.

However, even in the antibody and antibody molecule obtained by such a combinatorial method and genetic engineering approach, it is still difficult to obtain a clone having an excellent binding ability to a substance such as a sugar and a lipid, at present.

On the other hand, it has been suggested that the in-vivo behavior of a lipid and post-translational modification of a protein have biologically significant meanings. Therefore, it is expected to apply them to not only biochemical/medical fields but also wide variety of fields.

In recent years, attempts have been made to design and prepare a capturing molecule using an oligopeptide and a protein molecule other than an antibody or an antibody fragment. Such a candidate protein for use in a novel capturing molecule can be selected by a combinatorial method from a molecule library having molecular diversity genetically produced by taking an advantage of a stable molecular structure (J. Mol. Recognit., 2000, 13, 167-187). In most of these molecules, a β-sheet structure present in the molecules is used, more specifically, a loop structure which is considered less contributable to stabilization of the entire structure of the molecule between not less than two strands, is genetically manipulated to impart diversity. In this respect, diversification of these molecules is produced in the same manner as in an antibody. Furthermore, the mechanism for recognizing a target substance by a plurality of loops may be similar to that by an antibody. Representative examples of such a molecule include anticolin (Review in Molecular Biotechnology, 74: p 257, 2001), fibronectin and type III domain (J. Mol. Biol, 284:p 1141, 1998).

Recently, it is proposed that a molecule having an α-helix as a basic structure recognizes a target substance in a different mechanism from that of a β-sheet structure represented by an antibody (Nature Biotechnol. 15, 1998, 772-777, Nature Biotechnol, 2004, 22, 575-582, and WO0220565).

These publications disclose the results, which suggest that a molecule binds to a target substance via an amino acid residue exposed on the surface of an α-helix in contact with a solvent (also called as a solution contact surface or an exterior surface) or via an amino acid of the peptide portion connecting between the α-helices.

Furthermore, even among proteins having the same β-sheet structure as in an antibody, a molecule which binds to a target substance via a different mechanism from that involved in the loop structure of the antibody is disclosed, wherein a target substance is bound to a concave portion formed by side chains of a β-strand forming a β-sheet structure (Biochem. J., 2004, 382, 769-781).

As a more specific example, mention is made of CBM4-2 classified in a carbohydrate binding module.

The aforementioned technique suggests that a substance rarely recognized by an antibody known in the prior art can be recognized by a different molecular recognition mechanism from that of the antibody.

However, the binding ability of a substitute antibody molecule as described above to a target substance is generally low compared to that of the antibody to the antigen of an antibody-antigen complex. For example, lipocalin and fibronectin having a $K_D$ value to a target substance falling within several to several tens of nM are disclosed. A CBM as mentioned above generally has a $K_D$ value of several to several tens of μM. It is presumed that such binding abilities of these substitute antibody molecules are too low to produce a product having a desired ability sufficient to capture a target substance. When such a substitute antibody molecule is used in a sensor, an SN ratio of sensitivity, ascribed to the non-specific interaction between proteins, presumably increases. Therefore, even if a novel capturing molecule capable of capturing a substance that has a low binding ability to an antibody, the binding specificity of the novel capturing-molecule is not considered sufficient in view of application to a product. A technical problem still remains.

DISCLOSURE OF THE INVENTION

An object of the present invention is to provide a target-substance capturing molecule improved in productivity and binding ability to a target substance. In the present invention, to a domain using an antibody molecule or a domain binding to a target substance in the same binding manner as in an antibody, a domain binding to the target substance in a different manner as in an antibody is bound. Another object of the present invention is to provide a method of detecting a target substance by using a capturing molecule having the combination of domains binding to the target substance in different manners, and provide a kit for use in the detection method.

A target-substance capturing molecule according to the present invention is a capturing molecule having not less than two domains specifically binding to different sites of a target substance, wherein the not less than two domains comprise (1) a first domain having a hypervariable loop structure at the binding site to the target substance, and (2) a second domain having no hypervariable loop structure at the binding site to the target substance.

A method of detecting a target substance according to the present invention is a method of detecting a target substance characterized by comprising the steps of reacting the capturing molecule having the aforementioned structure with a specimen and detecting binding of the target substance and the capturing molecule when the specimen contains the target substance.

An apparatus for detecting a target substance according to the present invention is an apparatus for detecting a target substance, comprising the capturing molecule to be bound to the target, a detecting element having the capturing molecule provided on at least one portion of a surface thereof, holding means for holding the element, and detecting means for detecting the target substance by the element.

A kit for detecting a target substance according to the present invention is a kit for detecting a target substance, comprising the capturing molecule having the aforementioned structure, and a reagent for detecting the binding of the capturing molecule and a target substance.

In the present invention, not less than two domains specifically recognizing different points on a target substance include a first domain having a hypervariable loop structure at the binding site to the target substance and a second domain having no hypervariable loop structure at the binding site to the target substance. By this feature, a higher affinity than an antibody or an antibody fragment binding at an antigen determinant site (epitope) on the surface of a target substance can be imparted to a target-substance capturing molecule. In particular, since the domain having no hypervariable loop structure is used, the target-substance capturing molecule can bind to a surface amino acid residue, which rarely binds specifically to an antibody or an antibody fragment. As a result, the capturing molecule can acquire a binding ability (avidity) to a target substance that cannot bind to an antibody or an antibody fragment.

Furthermore, in the case where a capturing molecule according to the present invention is constituted of a single polypeptide chain, the molecular stability in various solutions can be improved. Moreover, in the case where a capturing molecule according to the present invention is constituted of not less than two different polypeptide chains, improved yields can be expected in steps of production and purification of individual polypeptide chains. Moreover, when a heavy chain variable region of an antibody is selected as the domain having a hypervariable loop structure, the molecular stability can be further improved. Furthermore, when an ankyrine structure is employed as the domain having no hypervariable loop structure, the molecular recognition mechanism can be further diversified.

BEST MODE FOR CARRYING OUT THE INVENTION

Figure 1:
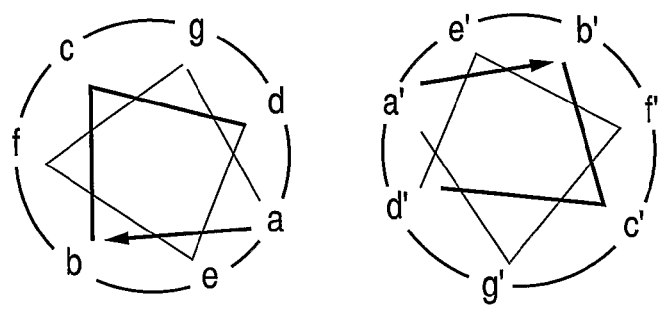
FIG. 1 is a view illustrating an α-helical coiled coil structure.

The present invention will be explained in detail below. The capturing molecule of the present invention has at least one first domain and at least one second domain serving as binding sites to a target substance. The first domain has a hypervariable loop structure at the binding site specifically binding to a target substance. The binding site having the hypervariable loop structure specifically recognizes a part of the target substance to bind to it. On the other hand, the second domain has a binding site specifically binding to the target substance by means of a structure except for the aforementioned hypervariable loop structure. The binding site of the second domain to the target substance specifically recognizes a part of the target substance (the recognition site by the second domain) to bind to it. The sites (recognition sites) of the target substance recognized by a plurality of domains consisting of the first and second domains differ. As a result, in a complex of the target substance and the capturing molecule, individual domains of the capturing molecule bind to the target substance at different sites.

Substances to be used as a constituent of a capturing molecule according to the present invention and a method for producing the substances will be further explained below.

(First Domain)

The first domain has a hypervariable loop structure at the binding site to a target substance.

(Loop Structure)

Generally, when the polypeptide chain having a plurality of loop formation sites discretely positioned thereon takes a secondary structure, they come to be sterically close to each other. The loop structure refers to such a state of a structure by which a target site of a target substance can be specifically recognized to bind to the target site. As such a loop structure, kunitz structure may be mentioned. Such a loop structure can be formed by introducing two Cys groups under oxidation conditions at appropriate positions of a polypeptide chain.

(Hypervariable Loop Structure)

The hypervariable loop structure generally refers to the following structure.

That is, when the polypeptide chain having a plurality of loop formation sites discretely positioned thereon takes a secondary structure, they come to be sterically close to each other. The hypervariable loop structure refers to such a state of the structure by which a target site of a target substance can be specifically recognized to bind to the target site.

Examples of such a hypervariable loop structure include a hypervariable loop structure (a complex structure of 3 loops) formed of portions containing a CDR region of an antibody and fibronectin III (a complex structure of 2 to 3 loops), and further include lipocalin (a complex structure of 4 loops). The hypervariable loop structure formed of portions containing a CDR region of an antibody can be obtained from a protein classified in an immunoglobulin superfamily.

The domains in the VH and VL of an antibody have a common framework formed of a sandwich structure of two antiparallel β-sheets. The loop structure positioned at the end of the β-sheet sandwich structure and serves as a recognition site, CDR. There are 3 loops in each domain of an antibody. The binding ability of each antibody domain to a target substance is determined by the nature and the number of the amino acid residues forming the loop, and their sterical configuration. The variability of amino acid sequences of the loop structure contributes to the binding diversification of antibody molecules. This region is called a hypervariable loop structure of an antibody.

(Immunoglobulin Superfamily)

The immunoglobulin superfamily refers to protein, which is analogous to an antibody in structure and function, found in the body fluid of a living creature from fish to mammals, and produced from the lymphocytes. As the hypervariable loop structure contained in the first domain, use may be preferably made of a hypervariable loop structure derived from an antibody belonging to the immunoglobulin superfamily. As a result that genetic engineering technique concerning an antibody fragment has been studied for a long time, a desired capturing molecule comes to be easily obtained. The antibody fragment herein refers to a partial region of a monoclonal antibody.

Specific examples of the antibody fragment of the present invention may include the following ones.

That is, the examples include a single domain antibody (dAb) formed of a heavy chain variable region (VH) or a light chain variable region (VL) and a variable fragment of antibody (Fv) formed of a VH and a VL, and further include single chain Fv (scFv), which is a single stranded polypeptide of the Fv, and moreover include disulphide stabilized Fv (dsFv), which is FV having a mutation introduced thereto so as to form a disulphide bond between a VH and a VL; and also include Fd, Fab' and Fab formed of a VH and CH1 (constant region 1 of an antibody).

The "Fab'" refers to an antibody fragment obtained by treating an antibody with a proteolytic enzyme such as papain. More specifically, it refers to an antibody fragment produced by digesting an antibody at positions before and after the disulphide bond present between two heavy chains (H chains) in the hinge region of the antibody.

For example, when IgG is treated with papain, the disulphide bond present between the two H chains in the hinge region is cleaved at an upstream position to obtain two homologous fragments, which has a light chain (L chain) fragment and a heavy chain (H chain) fragment bound via a disulphide bond at the C terminal region. These homologous antibody fragments each are called Fab'. A fragment suitable for the antibody fragment to be used in the present invention can be selected among them in view of productivity and stability as a binding capturing molecule to a target substance.

Furthermore, either a VH or a VL can be employed as the first domain of a single domain antibody (dAb). The VH or VL serves as a binding domain at which the antibody binds to an antigen. Each of the domains VH and VL has a common framework formed of a β-sheet sandwich structure of two antiparallel β-sheets.

When the hypervariable loop structure derived from an antibody or an antibody fragment is used as the first domain, a hypervariable loop structure capable of recognizing an epitope of a target substance to bind it, is preferably used. The amino acid sequence of a polypeptide chain for obtaining the hypervariable loop structure can be specified by a method using the immune system or the like. Furthermore, the amino acid sequence of the polypeptide chain thus specified may be modified as long as it can recognizes the epitope of the target substance to bind it, in other words, as long as the hypervariable loop structure is functional.

Preferable Embodiment of the First Domain

The first domain of a capturing molecule according to the present invention has a hypervariable structure. The structure having a hypervariable structure can be obtained by using at least one variable region of an antibody corresponding to a first epitope of a target substance. Alternatively, the first domain may be a hypervariable structure of an antibody corresponding to a first epitope of a target substance or a partial structure thereof containing at least one loop structure. Of them, the first domain is preferably a clone of a single VH or VL having a hypervariable loop structure and high molecular stability. In human antibody fragments, they are classified into sub families based on the amino acid sequence of a relatively common region called a framework and various differences in feature between subfamilies are disclosed by various studies so far made.

In view of these findings, an assembly of a DNA library can be prepared based on a stable framework such as VH3, which has been reported that the most stable molecular species is dominated. Subsequently, a DNA library of an antibody fragment having a stable framework of a variable region of an antibody is constructed and a gene encoding the CDR portion is chemically synthesized and introduced in the framework region. Such an approach may be employed. This approach is preferable since a CDR sequence not present in the nature can be created and in view of increasing the variety of the library. Alternatively, a first domain may be used by enhancing its stability by improving a factor making a molecule unstable, that is, a residue, more specifically, a hydrophobic amino acid residue present in a molecular surface such as the VH/VL interface. The aforementioned single domain structure is generally unstable in most cases, so that it may be stabilized by chemically modification with PEG. Furthermore, the dAb may be a variable region of a heavy chain of a camel antibody (VHH) (J. Mol. Biol, 311:p 123, 2001), which is present in vivo and functions as a heavy chain antibody, and a variable region IgNAR of an immunoglobulin-like molecule of nurse shark (Molecular Immunology, 2001, 38, 313-326). In particular, it is known that the variable region of a heavy chain of a camel antibody (VHH) has high molecular stability. Therefore, it may be present stably in a production/purification step and an industrially acceptable yield of VHH can be expected. The reason for such a heavy chain variable region of an antibody to exhibit molecular stability is considered as follow. As one of the reasons, mention may be made of a decreased ratio of a hydrophobic portion that is exposed in the heavy chain/light chain interface present in the variable region of an antibody formed of heavy chain/light chain. For example, a document (Biochemistry 2002, 41, 3628-3636) discloses that when the heavy chain variable region of a camel antibody is heated (80° C.) and kept cool at room temperature, the binding ability thereof can be recovered to 70 to 90%; on the other hand, when the heavy chain variable region of a human antibody is treated in the same manner, as a comparative example, it is aggregated. As described above, a heavy chain variable region in several antibodies of a camel is presumed to have a very stable molecular structure. Furthermore, antibodies of camel has an advantage wherein a heavy chain fragment of a camel antibody has resides in that the length of amino acids constituting CDR3 (one of three CDRs) is long. It is known that CDR3 of a murine H chain is composed of about 9 amino acids in average and CDR3 of a human H chain is composed of about 12 amino acids; in contrast, CDR3 of a camel is composed of about 18 amino acids. It has been suggested that the CDR 3 of H-chain of a camel is long in order to make up for deficiency of a light chain by increasing the number of amino acid residues, thereby compensating a decrease in degree of variety. Also, the H-chain CDR of a camel contributes to molecular stability by reducing the area of the hydrophobic region in contact with a solution. This site correspond to the heavy chain/light chain interface of human and murine antibody. Furthermore, it is suggested that the long CDR3 may bind to the valley present in an enzyme active center and bind to a low molecular compound, therefore, when an antibody fragment is singly used as a capturing molecule, camel antibody will be a useful candidate. To stabilize the structure of a heavy chain of an antibody as in the case of a camel described above, a mutation of an amino acid in connection with structural stability may be introduced into an antibody fragment of a mouse or human to stabilize the molecular. Alternatively, improvement of leading domain selected under a desired selection pressure may be performed by introducing a mutation by evolutional engineering. Such adoption of a structural feature of the heavy chain variable region of a camel antibody to a variable region of a mouse or human antibody formed of a heavy chain/light chain is possible. To describe more specifically, a mutation may be introduced into the VH/VL interface. A mutation may be introduced into any one of Val37Phe, Gly44Glu, Leu45Arg, and Trp47Gly (numerical value follows the Kabat Numbering, Sequence of Protein Immunological Interest, 5th edit, 1991).

(Second Domain)

The second domain has a binding site for binding to a second epitope of a target substance by means of a structure other than the hypervariable loop structure, as explained above. The second domain may be a target-substance binding domain selected from the group consisting of oligopeptides and protein molecules not classified in the immunoglobulin superfamily. The binding site of the second domain to a second epitope of a target substance may be selected from the group of known substitute antibody candidate molecules capable of specifically binding to a portion which is different from a first epitope of a target substance, on the basis of a desired binding ability to the target substance. For example, the binding site described in the document (Journal of Immunological Method, 2004, 290, 3-28) may be employed. The binding ability used herein includes not only the affinity for a target substance represented by an index such as $K_D$ when a complex with the target substance is formed, but also specificity sufficient to distinguish a family and a variant of a protein or a peptide when the target substance is the protein or the peptide. As a binding domain by which such a binding ability (specificity) is imparted to a target-substance capturing molecule according to the present invention, a binding domain having a different molecular recognition mechanism from that of the variable region of the antibody may be mentioned. Such a recognition mechanism may be mediated via an amino acid residue on a loop formed by an intramolecular disulphide bond and an amino acid residue dotted on the discontinuous region on the surface of a secondary structure of a protein, such as an α-helix or a β-sheet.

As the second domain, it is preferable to use a molecular species having not only a binding ability to a target substance but also productivity and molecular stability. In consideration of these points, the second domain preferably also has a structure having a low molecular weight with being easily folded and being rigid after folding. Furthermore, genes encoding the variable region can be diversified with a scaffold portion (basal portion or sticking place) for maintaining the structure and a variable region to which a mutation is to be introduced. By virtue of this, it is possible to construct a protein having the structure or the library of DNA encoding the protein. Using these, a binding species to be bound to a target substance can be selected by the aforementioned combinatorial method.

Preferable examples of the binding domain satisfying the aforementioned conditions and belong to a family other than the immunoglobulin superfamily include Z domain of protein A having a molecular recognition site formed of an α-helix, naturally occurring ankyrine, leucine-rich repeat, armadillo structure, tetratricopeptide structure, and HEAT structure (J. Mol. Biol., 2001, 309, 1-18), and further include structural proteins having these basic structures as a motif, Zinc finger, and Knott-in structure. According to the aforementioned references, various analyses have been made on capturing molecules consisting of ankyrine and a leucine-rich repeat with respect to the structure in capturing and function. In particular, it is reported that the residue of ankyrine interacting with a target substance is primarily present in part of the externally exposed surface of a β-hairpin and the first α-helix. It is shown that the residue interacting with a target substance can provide a large contact surface area for the interaction between the ankyrine molecule, which serves as a capturing molecule and is formed of ankyrine base structure repeats, with a target molecule. It is disclosed that, in such a binding manner, even if an amino acid residue responsible for the interaction between a capturing molecule and a target molecule and structural complementarity are not present, the surface stability can be facilitated by covering the peripheral amino acid residue of one of the capturing molecule and the target molecule by the other. According to this disclosure, a further synergetic effect may be expected. Such a binding manner cannot be observed when an antibody/antigen immune complex is formed. The binding manner is preferable since a target substance having a low binding affinity for an antibody known in the art may exhibit a higher binding affinity than that for the antibody known in the art. In a recombinant protein formed of such structure repeats, the molecular stability of the protein can be controlled by controlling the number of repeats of a unit structure. Therefore, it may be said that the recombinant protein is an excellent material from a molecular-design point of view.

Furthermore, the recombinant protein having an ankyrine structure is produced by culturing a general host cell, *Escherichia coli*, in an amount of several tens to several hundreds of mg/L. Therefore, the recombinant protein is also useful in view of productivity.

Furthermore, the binding site of the second domain to a target substance may have a structure having the β-sheet structure analogous to that of the immunoglobulin superfamily, wherein a target substance may be recognized not by a loop structure formed between β strands but by recognizing a sugar chain molecule by a "groove" portion formed of amino acid side chains constituting the strand, for example CBM (carbohydrate-binding module) does. Furthermore, the binding site may be a molecule selected from the Knott-in structure family, which is known to bind to a sugar and a lipid.

When the binding with a target substance is performed via the surface of a secondary structure in contact with a solvent, a part of the binding site may be present in the loop connecting to the secondary structure.

(The Form of Capturing a Target Substance by a Target-Substance Capturing Molecule)

In a target-substance capturing molecule according to the present invention, the binding site of the capturing molecule to the target substance is formed of at least one first domain and at least one second domain. Since the binding site has not less than two binding domains different in binding manner (first domain and second domain), a single capturing molecule may have multiple types of binding functions derived from a plurality of domains.

In the present invention, the binding functions derived from a plurality of domains of the capturing molecule may be used singly or in combination of two or more, simultaneously.

When binding functions derived from a plurality of domains are used simultaneously, a capturing molecule preferably has the plurality of domains, which almost simultaneously bind to different portions of a target substance noncompetitively to form a complex of the target capturing molecule and the target substance. In the complex of the target capturing molecule having plurality of domains bound to a target substance, not only $K_D$ values of individual binding sites but also ability of forming complex to the target substance (avidity) can be improved since $K_D$ values of individual binding sites synergistically work. Furthermore, since the second domain, which differs in binding specificity from that of the first domain, is added, stable complex can be formed for such a target substance that has been difficult to form a stable antigen-antibody complex with an antibody or an antibody fragment known in the art.

To form a complex in which a plurality of domains all bind to different sites of a target substance, a capturing molecule must have a sterical configuration enabling such a complex, in other words, a structure having such a plurality of domains formed therein.

As long as a capturing molecule having such a structure, the capturing molecule may have domains directly bound to each other or may be formed of a single stranded polypeptide chain, which is connected by use of a polypeptide linker. The linker may have an amino acid sequence known in the art, for example, a sequence repeat GGGGS derived from a fibrous phase frequently used in scFv or the like. The number of repeats of a sequence is preferably determined based on the coordination between binding domains and or between a target substance and a binding domain. Similarly as above, it is preferable that the aforementioned positional arrangement is satisfied and binding ability, productivity and stability are sufficient.

Furthermore, a molecule is constituted by arranging a single domain per polypeptide chain, and then a plurality of polypeptide chains having such a molecular constitution may be associated with each other to form a capturing molecule. In this case, it is necessary to prepare a polypeptide association portion between the polypeptide chains to allow polypeptide chains to associate with each other. Preferable association portion of the present invention will be explained in detail.

(Association Portion of Polypeptides)

When a target-substance capturing molecule according to the present invention is formed of not less than 2 polypeptide chains each having a single domain for binding to a target substance, each polypeptide chain has a polypeptide association portion for associating a polypeptide chain. The polypeptide association portion may be arranged at any position as long as it does not prevent the binding of a capturing molecule and a target substance to be formed. For example, in each binding domain, a polypeptide association site may differ from the position of binding site to a target. Furthermore, in each polypeptide chain, the binding domain binding to a target substance is discretely arranged from a polypeptide association portion as described above.

At such a polypeptide association portion, association may be mediated via a covalent bond or a non-covalent bond. The non-covalent bond used herein includes Van der Waals attraction, hydrogen bonding, ionic bonding, and hydrophobic interaction. These are due to the polypeptide association portion, in particular, an amino acid residue of the association portion.

According to the present invention, the polypeptide association portion is preferably a peptide having a complementary interaction. Any peptide may be used as the polypeptide association portion as long as it has a complementary interaction. More specifically, the peptide may be either an oligo peptide or a protein formed of a plurality of domains. More specifically, use may be made of an a domain and omega domain of β-galactosidase. Also, antibody fragments VH and VL may be used as the association portion and further α-helical coiled coil structure, which is frequently observed in naturally occurring protein structure, may be used. The α-helical coiled coil structure is formed of several α-helix chains mutually interacted (associated) and wound. Two rounds of a helix are formed of 7 amino acid residues. The positions of 7 amino acid residues are usually indicated by a, b, c, d, e, f, and g as shown in FIG. 1. Hydrophobic amino acids such as Val and Ile, Glu, Lys, Gln, and Arg, which play a important role in associating helices, are used as amino acids a and d. Of them, Val and Ile are desirably used. The α-helix coiled coil may be formed of a plurality of α-helix chains depending upon the amino acids selected as those of the association surface. Alternatively, formation of the coiled coil structure may be induced by introducing His to the positions a and d in the co-presence of metal ions such as Co(II) and Ni(II).

As a model structure of the polypeptide association portion, mention may be made of a transcription factor GCN4 formed of a peptide having several amino acid repeats, and leucine zipper such as oncogene Fos and Jun. In the capturing molecule of the present invention, since the first binding domain and the second binding domain each bind to a different site of a target substance, α-helical coiled-coils that are fused with the first binding domain and the second binding domain are desirably to rarely form a homodimer. In this sense, the α-helical coiled-coils desirably form a hetero dimer such as Jun and Fos and a hetero polymer. Furthermore, it is known that a stable hetero coiled coil is formed by employing Glu in the positions e and g of the α-helical coiled coil to be fused with the first binding domain and Lys in the positions corresponding to these positions of the second binding domain.

Furthermore, a polypeptide association portion can be formed of polypeptide chains having oppositely charged.

It is necessary for such a polypeptide association portion to have a size required so as not to prevent production of each polypeptide chains and formation of a structure required for binding of a binding domain with a target substance. More specifically, the polypeptide association portion preferably has 50 or less amino acids, and more preferably, 15 to 35 amino acids. When detection is performed by a surface plasmon resonance method, which is described later, in particular, a local surface plasmon resonance method, the polypeptide association portion may be designed so as to have a length of the molecular falling within the optimal range corresponding to the distribution and intensity of the spatial electric field generated in a detective element to improve a sensitivity of the detective element.

Forming covalent bonding at the polypeptide association portion or it peripheral portion is an efficient means in view of stabilizing a capturing molecule according to the present invention. For example, an intramolecular disulphide bond may be formed by introducing Cys into a predetermined position.

Such a bond can be formed between amino acid positions a and d, or g and e. When forming at least one of the intramolecular disulphide bonds, it is desirable that the formation of the bond does not prevent binding of the binding domain to a target substance and also does not effect on the association of the peptides. To explain more specifically, in the case of a double stranded α-helical coiled coil, it is known that the disulphide bond formed between positions a-a is less stable in view of energy than the disulphide bond formed between positions d-d. In the case of more than three, introduction may be appropriately and selectively made. Furthermore, in accordance with the aforementioned way of thinking, a non-naturally occurring amino acid (synthetic amino acid), which is modified with an optimal linking group or has an optimal linking group introduced therein, may be introduced. In this case, a single optical functional group may not be introduced into each of all polypeptides to be associated. In other words, a single optical functional group is desirably introduced to the association portion between at least two polypeptide chains and its periphery of the association portion. When a polymer is formed of not less than three polypeptide chains, the introduction position of an optical function group may be appropriately studied in view of the arrangement of the three polypeptide chains.

In designing, the polypeptide association portion is preferably arranged so as not to prevent the binding between a binding domain and a target substance. More specifically, when the antibody fragment is used as the binding domain, in general, the polypeptide association portion is preferably fused at the C terminal of the antibody fragment and expressed as a fusion protein. The binding domain and the polypeptide association portion may be directly ligated to each other or ligated via a linker formed of a polypeptide chain. As the linker, use may be made of the hinge region of an antibody such as a human antibody, or a peptide sequence having a GGGGS sequence derived from a phage as a sequence repeat unit or at least containing a GGGGS sequence as described above.

(Method for Preparing a Capturing Molecule)

Now, a method for preparing a capturing molecule according to the present invention will be explained. A capturing molecule according to the present invention or polypeptide chains, which is constituents of the capturing molecule, can be synthesized as follows.

A host cell for expressing a known protein is transformed with an expression vector for a desired protein designed in accordance with the host cell. The desired protein can be synthesized by use of a protein synthesis system within the host cell. Thereafter, the desired protein, which is synthesized in the host cell and secreted outside the cytoplasm, is purified from either the intracellular fraction or a cell-culture supernatant and recovered. When a secretion-type expression system is used, since a desired protein can be obtained from the culture supernatant or the periplasm, the purification step of the protein can be simplified.

In most cases, under the reducing conditions of a cell, a stable active-form (folded) protein is rarely obtained. However, a desired stable and active-form folded protein can be obtained extracellularly (in culture supernatant) and in the periplasm by using a secretion type expression system. Therefore, the secretion type expression system is preferably used as a method for expressing and stably obtaining, for example, an active-form protein having an intramolecular disulphide bond. Furthermore, when an active-form recombinant protein is intracellularly expressed in a high level, the recombinant protein may be converted into insoluble granules (inclusion body) within a cell. Therefore, the expressed protein is preferably secreted outside the cell immediately upon production and kept at a concentration at which no aggregation takes place.

For example, when *Escherichia coli* is used as a host cell, a desired protein can be expressed and secreted outside the cytoplasm through the Sec system responsible for extracellular secretion by arranging a nucleic acid encoding a signal peptide known in the art and represented by pelB at the 5' side of a nucleic acid encoding the desired protein. Furthermore, it is possible to arrange a portion that encodes a plurality of polypeptide chains serving as constituents of a capturing molecule according to the present invention, in a single expression vector. In this case, by arranging the nucleic acid encoding pelB at the 5' side of each of the nucleic acids encoding individual polypeptide chains serving as constituent elements extracellular secretion can be promoted upon expression.

As described above, a polypeptide chain according to the present invention having a signal peptide fused to the N' terminal can be purified from a periplasm fraction and a culture supernatant fraction.

Another method is known as a method for extracellularly secreting a protein in the similar manner. That is a method using not the Sac secretion system as described above but the twin-arginine-translocation (TAT) system. This method may be useful for a protein, which is folded into an active form in the cytoplasm. As the signal peptide, use may be made of a conventional signal peptide containing two Arg residues. Other than this, use may be made of a method using a signal peptide fused with a known protein Dsb system localized in the periplasm.

In this case, purification may be made in accordance with the following method. That is, a protein component is concentrated from the culture supernatant and the periplasm fraction and thereafter resuspended in an appropriate buffer.

Subsequently, a His-tag, which is a conventional tag for purification of a recombination protein, is inserted into the N or C terminal of a desired protein and loaded into a metal chelate column using nickel or the like. In this manner, a desired protein can be purified.

Furthermore, in the case where a desired active-form protein can be expressed in a high concentration, the desired protein may be obtained by intracellularly expressing the protein, breaking the cells and extracting the protein from a fraction having the cytoplasm dissolved therein. In the purification method, a recombination protein purification tag known in the art such as GST-tag other than the His-tag may be used. Since the GST is a highly soluble protein even by itself, a desired protein expected to effectively dissolves when it is fused with GST. A polypeptide chain according to the present invention intracellularly expressed can be obtained in the form of insoluble granule. In this case, the bacterial cells obtained from a culture solution are broken by French press or ultrasonic wave, and the resultant solution containing broken bacterial cells is centrifugally separated to obtain the insoluble granules. The insoluble granule fraction thus obtained is dissolved in a buffer solution containing a conventional denaturing agent such as urea and a guanidine hydrochloride salt and then purified by a column under denaturation conditions, in the same manner as described above. The elution fraction obtained from the column is subjected to a refolding process. In this manner, the denaturing agent can be removed and the protein can be refolded into an active form. Refolding can be performed appropriately by selecting from methods known in the art, for example, stepwise dialysis and dilution known in the art in accordance with a desired protein.

In another preparation method, a desired protein may be expressed in vitro by using a cell extraction solution. As suitable cells used in this method, mention may be made of *Escherichia coli*, wheat germ, and rabbit reticular cells, etc.

However, protein synthesis using a cell-free extraction solution as mentioned above is generally performed under reducing conditions. Therefore, if necessary, some treatment is preferably applied to form an intramolecular disulphide bond.

In the case where a capturing molecule is formed by associating a plurality of polypeptide chains, individual polypeptide chains may be expressed either in the same host cell. Alternatively, the polypeptide chains may be expressed in different host cells, then coexisted and associated with each other to form a complex.

Furthermore, the present invention includes a nucleic acid encoding a polypeptide chain serving as a capturing molecule according to the present invention and an expression plasmid containing the nucleic acid.

(Target Substance)

The target substances serving as an object captured by a capturing molecule according to the present invention are roughly divided into non-biological substances and biological substances.

Examples of the non-biological substances that appear to be industrially variable include PCBs different in number and position of chlorine replaced and known as a pollutant; dioxins different in number and position of chlorine replaced; and endocrine disrupting chemicals called environmental hormones, such as hexachloro benzene, pentachloro phenol, 2,4, 5-trichloro acetic acid, 2,4-dichlorophenoxy acetic acid, amitrole, atrazine, arachlor, hexachlorocyclohexane, ethyl parathion, chlordane, oxychlordane, nonachlor, 1,2-dibromo-3-chloropropane, DDT, kelthane, aldrin, endrin, dieldrin, endosulfan (benzoepin), heptachlor, heptachlor epoxide, malathion, methomyl, methoxychlor, mirex, nitrophene, toxaphene, trifluralin, alkylphenol (having 5 to 9 carbon atoms), nonyl phenol, octyl/nonylphenol, 4-octylphenol, bisphenol A, di-2-ethylhexyl phthalate, butylbenzyl phthalate, di-n-butyl phthalate, dicyclohexyl phthalate, diethyl phthalate, benzo(a)pyrene, 2,4-dichlorophenol, di-2-ethylhexyl adipate, benzophenone, 4-nitro toluene, octachlorostyrene, aldicarb, benomyl, kepone (chlordecone), manzeb (mancozeb), maneb, metiram, metribuzin, cypermethrin, esfenvalerate, fenvalerate, permethrin, vinclozolin, zineb, ziram, dipenthyl phthalate, dihexyl phthalate, and dipropyl phthalate.

An applicable biological substance may be nucleic acids, proteins, saccharides, lipids, and complexes of these and further substances containing a biological molecule selected from the group consisting of a nucleic acid, protein, saccharide, and lipid. More specifically, the biological substance may contains a substance selected from any one of DNA, RNA, aptamer, gene, chromosome, cellar membrane, virus, antigen, antibody, lectin, hapten, hormone, receptor, enzyme, peptide, and sphingoglyco and sphingolipid. Furthermore, bacteria and cells themselves which produce the "biological substance" may be used as the "biological substance" serving as a target substance according to the present invention.

Specific examples of the protein used herein include disease markers such as

α-fetoprotein (AFP), which is an acidic glycoprotein produced in the liver cells during the fetus period and present in the fetus blood, serving as a marker of hepatic carcinoma, (primary hepatic carcinoma), hepatoblastoma, metastatic hepatic carcinoma and yolk sac tumor;

PIVKA-II, which is an abnormal prothrombin emerging when the liver is substantially damaged and observed specifically in hepatic carcinoma;

BCA225, which is a glycoprotein immunohistochemically serving as a breast cancer specific antigen, serving as a marker of progressive primary breast cancer, and recurrent/metastatic breast cancer;

basic fetoprotein (BFP), which is a basic fetus protein found in the serum and an extraction solution from the intestine and blain tissue of a human fetus, serving as a marker of ovarian cancer, testicular tumor, prostatic carcinoma, pancreatic carcinoma, carcinoma of the biliary tract, hepatic carcinoma, kidney cancer, lung cancer, gastric carcinoma, bladder carcinoma, and large bowel cancer;

CA15-3, which is a sugar chain antigen, serving as a marker of progressive breast cancer, recurrent breast cancer, primary breast cancer, and ovarian cancer;

CA19-9, which is a sugar chain antigen, serving as a marker of pancreatic carcinoma, carcinoma of the biliary tract, gastric carcinoma, hepatic carcinoma, large bowel cancer, and ovarian cancer;

CA72-4, which is a sugar chain antigen, serving as a marker of ovarian cancer, breast cancer, carcinoma of the colon and rectum, gastric carcinoma, and pancreatic carcinoma;

CA125, which is a sugar chain antigen, serving as a marker of ovarian cancer (in particular, serous cystadenocarcinoma), adenocarcinoma of the uterine body, cancer of fallopian tube, adenocarcinoma of the uterine cervix, pancreatic carcinoma, lung cancer, and large bowel cancer;

CA130, which is a glycoprotein, serving as a marker of epithelial ovarian cancer, cancer of fallopian tube, lung cancer, hepatic carcinoma, and pancreatic carcinoma;

CA602, which is a core protein antigen, serving as a marker of ovarian cancer (in particular, serous cystadenocarcinoma), adenocarcinoma of the uterine body, and adenocarcinoma of the uterine cervix;

CA54/61(CA546), which is a core unit sugar chain related antigen, serving as a marker of ovarian cancer (in particular, mucous cystadenocarcinoma), adenocarcinoma of the uterine cervix, and adenocarcinoma of the uterine body;

carcinoembryonic antigen (CEA), which is presently most widely used for assisting cancer diagnosis as a tumor associated marker antigen of large bowel cancer, gastric carcinoma, rectal cancer, carcinoma of the biliary tract, pancreatic carcinoma, lung cancer, breast cancer, uterine cancer, and urinary tract cancer;

DUPAN-2, which is a sugar chain antigen, serving as a marker of pancreatic carcinoma, carcinoma of the biliary tract, hepatic carcinoma, gastric carcinoma, ovarian cancer, and large bowel cancer;

elastase 1, which is present in the pancreas and a proteolytic enzyme of a protein secreted outside the pancreas specifically hydrolyzing elastic fiber, elastin of the connective tissue (constituting such as aortic wall and tendon), serving as a marker of pancreatic carcinoma, cancer of the pancreatic cysts and carcinoma of the biliary tract;

immunosuppressive acidic protein (IAP), which is a glycoprotein present in the ascites and the serum of a human cancer patient in a high concentration, serving as a marker of lung cancer, leukemia, carcinoma of esophagus, pancreatic carcinoma, ovarian cancer, kidney cancer, carcinoma of the biliary tract, gastric carcinoma, bladder cancer, large bowel cancer, thyroid cancer, and malignant lymphoma;

NCC-ST-439, which is a sugar chain antigen, serving as a marker of pancreatic carcinoma, carcinoma of the biliary tract, breast cancer, large bowel cancer, hepatic carcinoma, adenocarcinoma of lung, and gastric carcinoma;

γ-semino protein (γ-Sm), which is a glycoprotein, serving as a marker of prostatic cancer;

prostatic specific antigen (PSA), which is a glycoprotein extracted from the prostatic tissue of a human and present only in the prostatic tissue, serving as a marker of prostatic cancer;

prostatic acidic phosphatase (PAP), which is an enzyme secreted from the prostate and hydrolyzes a phosphate ester under acidic pH, serving as a tumor marker of prostatic cancer;

nerve specific enolase (NSE), which is a glycolytic enzyme specifically present in the nerve tissue and nerve endocrine cells, serving as a marker of lung cancer (in particular, pulmonary lobule cancer), neuroblastoma, cancer of the nerve system, islet cell tumor, cancer of esophageal small cell, gastric carcinoma, kidney cancer, and breast cancer;

squamous cell carcinoma associated antigen (SCC antigen), which is a protein extracted and purified from hypatic metastatic cancer transferred from squamous cell carcinoma of the uterine cervix, serving as a marker of uterine cancer (squamous cell carcinoma of the uterine cervix), lung cancer, esophageal cancer, cancer of head and neck, and skin cancer;

Sialyl Le$^x$-i antigen (SLX), which is a sugar chain antigen, serving as a marker of adenocarcinoma of lung, carcinoma of esophagus, gastric carcinoma, large bowel cancer, rectal cancer, pancreatic cancer, ovarian cancer, and uterus cancer;

SPan-1, which is a sugar chain antigen, serving as a marker of pancreatic carcinoma, carcinoma of the biliary tract, hepatic carcinoma, gastric cancer, and large bowel cancer;

tissue polypeptide antigen (TPA), which is a single chain polypeptide, serving as a marker of carcinoma of esophagus, gastric carcinoma, carcinoma of the colon and rectum, breast cancer, hepatic carcinoma, carcinoma of the biliary tract, pancreatic carcinoma, lung cancer, and uterine cancer, and useful in estimating a progressive cancer in combination with other tumor markers, and in recurrent prognosis/follow-up checking;

Sialyl Tn antigen (STN), which is a core unit sugar chain antigen, serving as a marker of ovarian cancer, metastatic ovarian cancer, gastric carcinoma, large bowel cancer, carcinoma of the biliary tract, pancreatic carcinoma, and lung cancer;

CYFRA (cytokeratin), which is a tumor marker useful for detecting pulmonary lobule cancer of lung, in particular, squamous cancer of lung;

pepsinogene (PG), which is an inactive precursor of two types of pepsin (PG I•PG II), proteopepsis secreted into the gastric juice, serving as a marker of gastric ulcer (in particular, low level gastric ulcer), duodenal ulcer (in particular, recurrent and hard-to-cure), adenoma of the Brunner gland, Zollinger-Ellison Syndrome, and acute gastritis;

C-reactive protein (CRP), which is an acute phase reactive protein whose level changes in the blood plasma due to tissue damage and infection, and whose level increases when necrosis of the cardiac muscle is caused due to acute cardiac infarction;

serum amyloid A protein (SAA), which is an acute phase reactive protein and whose level changes in the blood plasma due to tissue damage and infection;

myoglobulin, which is a heme protein having a molecular weight of about 17500 and present primarily in the cardiac muscle and skeleton muscle, serving as a marker of acute cardiac infarction, muscular dystrophy, multiple myositis, and dermatomyositis;

creatine kinase (CK) (including three types of isozymes, CK-MM type derived from the skeleton muscle, CK-BB type derived from the brain and smooth muscle, and CK-MB type derived from the cardiac muscle; mitochondrial isozyme, and CK binding to immunoglobulin (macro CK)), which is an enzyme primarily present in a soluble fragment of the skeleton muscle and the cardiac muscle and released into blood by cell damage, serving as a marker of acute cardiac infarction, hypothyroidism, progressive muscular dystrophy, and multiple myositis;

troponin T, which is a protein having a molecular weight of 39,000, forming a troponin complex with troponin I and troponin C on a thin filament of the striated muscle, thereby relating to regulation of contraction of the muscle, serving as a marker of rhabdomyolysis, myocarditis, cardiac infarction, and renal failure;

ventricle myosin light chain I, which is a protein contained in both the skeleton muscle and the cardiac muscle, serving as a marker of acute cardiac infarction, muscular dystrophy, and renal failure, since an increased level of ventricle myosin light chain I means damage of the cardiac muscle and necrosis; and chromogranin A, thioredoxin, and 8-OhdG, which have been, recently attracted attention as a stress marker.

A method for detecting a target substance using a capturing molecule according to the present invention include a step of reacting the capturing molecule with a specimen and detecting binding of the target substance and the capturing molecule when the target substance is contained in the specimen.

A kit for detecting a target substance according to the present invention has a capturing molecule and a reagent for detecting the binding between the capturing molecule and the target substance. The kit for detecting a target substance may further have a reagent and a element for reacting the capturing molecule with the target substance, and a element for detecting the binding between the capturing molecule and the target substance where necessary. A detection method of the target substance and a element and a reagent for use in the method will be described below.

(Detection Kit)

A capturing molecule according to the present invention can be used for capturing a target substance and applicable to various uses employing the step of capturing a target substance. In particular, a capturing molecule according to the present invention can be preferably used in a detection method and a kit for detecting a target substance.

(Sensor Element)

As a sensor element according to the present invention, use may be made of various sensor elements known in the art.

However, sensor elements using a surface plasmon resonance method and a local surface plasmon resonance method are preferable since a label molecular such as fluorescent pigment is not required and proceeding of the binding reaction between a target substance and a capturing molecule can be monitored in real time. Particularly, detection performed by the local surface plasmon resonance method can be made by a detection element having a simple structure in which fine metal particles are fixed on the surface of a substrate. In such a sensor element, change caused by desorption and absorption of a substance taking place in the vicinity of the surface of the fine metal particles can be expressed in terms of change in dielectric constant, which is further observed in terms of change in optical characteristics (an absorption change at a predetermined wavelength or shift in an absorption-peak).

A preferable detection element for use in a local surface plasmon sensor is a target substance detection element having a substrate, a sensor element which is formed of a metal construct provided on the surface of the substrate for generating local surface plasmon resonance, and a target substance capturing body arranged on the metal construct.

(Metal Construct)

The metal construct of the present invention can be appropriately selected from those generating a local surface plasmon resonance. Examples of such a metal construct include fine metal particles arranged on a substrate and a metal thin film pattern formed on a substrate. The metal constructs are preferable since the shape of the metal construct formed on a substrate can be easily controlled and variation in measurement value by a sensor element can be minimized.

(Fine Metal Particles)

Any fine metal particles may be used as long as the particles contain a metal possibly generating a plasmon resonance phenomenon. As such a metal, gold, silver and copper are preferable. Particularly, silver is preferably used since it is excellent in sensitivity although low in corrosion resistance. Gold is also preferably used since it has advantages such that corrosion resistance is high so that a stable detection element can be manufactured, and that surface modification and immobilization with a thiol group and an amino group can be easily made. The fine metal particles can be immobilized by using a substrate whose surface is treated with an amino group or thiol group. The immobilization density may be controlled by the content of the fine metal particles in a fine metal particle solution.

(Metal Thin Film Pattern)

As a material for use in the metal thin film pattern, use may be made of a metal selected from the group consisting of gold, silver, copper and aluminium or an alloy of these. The metal thin film pattern is formed of metal dots (convex-form) aligned on a substrate or holes (concave-form) aligned in a metal thin film substrate. The shape of dots and holes may be circle, regular square, triangle, and rectangle; however may not be limited to these.

The metal pattern may be formed on a substrate via chromium or titanium thin film in view of adhesiveness to the substrate.

The metal pattern may preferably be formed with a film thickness of about 10 nm to 200 nm.

The size of the plan shape of the metal pattern, in other words, the distance from an arbitral point on the outer periphery to another point preferably fall within the range of 10 nm to 1450 nm, and further preferably, 50 nm to 450 nm. In this case, the largest distance between the arbitral two points may fall within the aforementioned range.

If necessary, not less than one metal pattern may be formed on a substrate. When a plurality of metal patterns are formed, the intervals between metal constructs preferably fall within the range of 50 nm to 2000 nm, and more preferably, 150 nm to 1000 nm. This is because the interaction due to plasmon takes place between metal constructs and influences the spatial distribution and intensity of an electric field. Furthermore, if the interval between metal constructs increases, the density of metal constructs decreases, and the intensity of a signal decreases, with the result that a special optical system must be used. Therefore, it is preferable that the interval between metal constructs falls within the aforementioned range.

A plurality of metal constructs can be formed on a substrate. More specifically, multiple types of metal constructs different in at least one of a plan shape and size may be formed on a substrate.

(Substrate)

As a material for a substrate used in the present invention may be selected from the group consisting of materials that can form a metal construct selected from the aforementioned constructs and having optical characteristics that allow detection by a plasmon resonance method. Examples of such a material include a glass substrate, quartz substrate, and plastic substrate such as polycarbonate and polyethylene terephthalate.

(Method of Producing a Sensor Element)

A method for producing a sensor element of a metal thin film pattern according to the present invention will be described. First, a metal thin film is formed on a substrate by a sputtering method or deposition method. On the thin metal film, an electron beam resist is formed by spin coating, exposed to the electron beam applied by means of an electron beam lithography apparatus, and developed to obtain a resist pattern. Thereafter, an unnecessary metal thin film is etched away. In this manner, a resist is removed to obtain a metal construct arranged in the form of desired well. Patterning can be made by an apparatus other than the electron beam lithography apparatus, such as a focused ion beam processing apparatus, X-ray exposure apparatus, and EUV exposure apparatus. Such a sensor element can be formed using a substrate having minute convexoconcave portions, which are formed by a molding method. In this case, a metal thin film is formed on a substrate by a sputtering method or a deposition method. Subsequently, the metal thin film of the substrate surface is polished to form a desired metal construct on the substrate.

(Method of Immobilizing a Capturing Molecule)

The immobilization method used herein may be selected from the group consisting of physical adsorption methods and chemical crosslinking methods known in the art. In view of using a capturing molecule on the element efficiently, it is preferable to employ an immobilization method capable of providing an orientation. An example of the immobilization method includes introduction of Cys into the C terminal of a polypeptide chain constituting a capturing molecule according to the present invention. When the surface of the sensor element is made of gold (Au), the orientation can be given by coordination of gold-thiol. When coating is applied in order to prevent non-specific adsorption of a protein onto the surface of a sensor element, processing is made such that a maleimide group can be coordinated on the surface of the coating. In this manner, a capturing molecule can be immobilized.

When a capturing molecule is immobilized by use of the Cys residue introduced into the C terminal, the capturing molecule is preferably designed to have a domain of a binding site to a target substance, and the association portion of polypeptide chains which do not have Cys residues, or to have less effect of Cys residue introduced for use in binding to the substrate produces. If such a domain or the like has Cys, a disulphide bond may be formed at an undesirable position under acidic conditions, raising problems of productivity and yield.

On the other hand, a peptide and an antibody fragment having affinity for a surface material of a substrate may be fused with the N terminal or the C terminal of a capturing molecule according to the present invention. As such a affinity peptide, use may be made of various types of peptides known in the art such as the peptides described in Nature Materials, Vol. 2, pp 577, 2003). A method of fusing a capturing molecule includes steps of inserting a nucleic acid encoding the affinity peptide into the 5' end or the 3' end of a nucleic acid encoding a peptide chain constituting a capturing molecule, and inserting the nucleic acid obtained above into an expression vector to produce a fusion protein. In a method of using an antibody fragment, an antigen against an antibody used as an immobilization tag may be immobilized onto a sensor element in advance.

The antibody fragment recognizing the surface of a sensor element may be used. More specifically, the antibody fragment is arranged at a position that will not prevent the binding between a capturing molecule and a target substance. In this manner, the capturing molecule can be immobilized onto the surface of the sensor element. As such an antibody fragment, use can be made of VH and VL of an antibody recognizing the surface of a sensor element. When the capturing molecule is constituted of a plurality of polypeptide chains associated with each other, the following method can be employed.

That is, VH having affinity for the surface of a sensor element is arranged at an end of an association portion of a polypeptide chain. To the association portion of another polypeptide chain to be associated with the aforementioned polypeptide chain, VL complementary with the VH and having affinity for the surface of the sensor element is provided directly or via a peptide linker. In this manner, a plurality of polypeptide chains are associated with each other to produce a capturing molecule and simultaneously immobilized onto the surface of the sensor element.

When detection is made by a surface plasmon resonance method, in particular, a local surface plasmon resonance method, it is more desirable to design the immobilization portion of the substrate such that a capturing molecule according to the present invention can capture a target molecule within the most suitable range dealing with the spatial distribution and intensity of the electric field generating over the detection element.

On the surface of a detection element, coating can be made in the following manner in order to prevent signal generation caused by contaminants adsorbed nonspecifically. That is, the surface is coated with skim milk, casein, bovine serum albumin, phospholipid, or polyethylene glycol so as not to cover the exposed portion serving as the binding site and inhibit free movement of a capturing molecule according to the present invention.

(Detection Apparatus)

A detection apparatus for a target substance may have a structure in accordance with a detection system for the binding between a capturing molecule and the target substance. To describe more specifically, when the aforementioned detection element is formed of gold colloid, a detection apparatus may be constituted of a detection element having a metal construct and a detection means for detecting a signal from the detection element. The detection means may have an optical detection system constituted of a light source, a beam splitter and lenses, and a liquid feeding system constituted of a reaction well for performing a reaction with the detection element, and flow channel and liquid feeding mechanism for feeding a specimen (sample) to the detection element. The light source used herein preferably emits light covering the wavelength range from the visible light to infrared light. Optical determination can be made by use of an absorption spectrum, transmittance spectrum, diffusion spectrum, and reflection spectrum, and most preferably, a peak wavelength of the absorption spectrum or the intensity of the peak absorption is used. When the detection element having a metal construct specifically binds to a target substance, the peak wavelength of the adsorption spectrum shifts toward the longer wavelength side, and the absorption intensity increases. Based on degree of the shift amount and with reference to a calibration curve previously prepared by using the target substance, the amount of the target substance can be determined. Since the detection element of the present invention uses local plasmon resonance, the electric field is locally enhanced in the vicinity of the metal construct. This phenomenon can be also applied to the surface enhanced Raman spectrometry (SERS) and surface plasmon fluoro-spectrometry (SPFS). Quantitative determination of a target substance can be performed by these methods.

The reaction well and flow channel can be easily manufactured by a polydimethyl siloxane (PDMS) substrate used in an apparatus of a μTAS (micro total analysis system) type. To explain more specifically, the PDMS substrate is adhered to the substrate on which a detection element is formed to construct the structure shown in FIG. 7 for use in practice. As the liquid feeding mechanism, a micro piston pump and a syringe pump may be used.

EXAMPLES

The present invention will be more specifically explained below by way of Examples, which will not be construed as limiting the present invention.

Example 1

Preparation of Maltose-Binding Protein (MBP) Bound VHH-Encoding DNA Fragment

The DNA is synthesized by an over-lap PCR with reference to the sequences (Sequence ID Nos. 1 and 2) of MBP bound VHH. The PCR is performed by using a pfu-turbo kit (manufactured by Stratagene) in accordance with the method recommended by the manufacturer. Restriction site of NcoI is constructed at the 5' end and restriction site of EcoRI at the 3' end. The obtained PCR fragment is designated as MVHH (Sequence ID Nos. 3 and 4).

```
                                    Sequence ID No. 2
    QVQLQESGPGLLKPSETLFLTCTVSGFSISGGYYWGWFRQPPGKE

REWIGSVYHSGSTYYNKSLESRVTISIHTSESQISLKLNSVTAADTAVYSC

ARYRTAHPLWGQGTMVTVSS

Sequence ID No. 4
    PWQVQLQESGPGLLKPSETLFLTCTVSGFSISGGYYWGWFRQPPG

KEREWIGSVYHSGSTYYNKSLESRVTISIHTSESQISLKLNSVTAADTAVY

SCARYRTAHPLWGQGTMVTVSSEF
```

Example 2

Preparation of MBP-Bound Ankyrine-Encoding DNA Fragment

DNA of MBP-bound ankyrine is synthesized by an overlap PCR known in the art with reference to the sequences of DDBJ accession No. AY326424 (Sequence ID Nos. 5 and 6). The PCR is performed by using a pfu-turbo kit (manufactured by Stratagene) in accordance with the method recommended by the manufacturer. A primer is designed so as to introduce restriction site of EcoRI at the 5' end and restriction site of HindIII at the 3' end. Furthermore, a linker sequence consisting of three repeats of a GGGGS sequence is provided at the 5' end of the MBP bound ankyrine gene sequence (Sequence ID Nos. 7 and 8).

```
                                    Sequence ID No. 6
    NAADNTGTTPLHLAAYSGHLEIVEVLLKHGADVDASDVFGYTPLH

LAAYWGHLEIVEVLLKNGADVNAMDSDGMTPLHLAAKWGYLEIVEVLLKHG

ADVNAQDKFGKTAFDISIDNGNEDLAEILQ

Sequence ID No. 8
    EFGGGGSGGGGSGGGGSNAADNTGTTPLHLAAYSGHLEIVEVLLK

HGADVDASDVFGYTPLHLAAYWGHLEIVEVLLKNGADVNAMDSDGMTPLHL

AAKWGYLEIVEVLLKHGADVNAQDKFGKTAFDISIDNGNEDLAEILQRL
```

The obtained PCR fragment is designated G3-ank.

Example 3

Preparation of an Expression Plasmid of MBP-Bound VHH-Ankyrine Fusion Protein

Using the PCR fragments obtained in Example 1 and Example 2, an expression plasmid of VHH-ankyrine fusion protein is prepared. The vector used herein is pET-24d (manufactured by Novagen).

(1) MVHH obtained in Example 1 and pET-24d are digested by restriction enzymes NcoI and EcoRI (both are manufactured by New England Biolabs) in the method recommended by the manufacturer and described in the technical bulletin.

(2) The resultant solution containing enzyme reaction products is subjected to agarose gel electrophoresis.

(3) An about 0.4 kbp fragment is cleaved out from a reaction product in a reaction MVHH solution and a 5.3 kbp fragment from a pET-24d reaction solution and purified by a purification kit (manufactured by Promega, trade name: Wizard SV Gel and PCR Clean-Up System).

(4) The DNA fragments obtained above are ligated with T4-Ligase (manufactured by Roche) for 2 hours in accordance with the method recommended by the manufacturer.

(5) JM109 competent cells (manufactured by Promega) are transformed by use of the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant culture solution and cultured at 37° C. for 1 hour while shaking. The obtained solution is centrifuged at 6000 rpm for 5 minutes and 700 µL of the supernatant is discarded.

(6) The remaining culture solution and the precipitate are stirred, spread on an LB/ampicillin (100 µg/mL) agar plate, and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the plasmid thus obtained is analyzed and checked whether a desired DNA fragment is inserted or not. The plasmid obtained herein is designated as PET-MVHH.

(10) The PET-MVHH thus obtained and DNA fragment, G3ank, are digested with restriction enzymes EcoRI and HindIII (both are manufactured by NEB) in accordance with the method recommended by the manufacturer.

(11) The resultant solution containing enzyme reaction products is subjected to agarose gel electrophoresis.

(12) An about 0.5 kbp fragment is cleaved out from the reaction product in a G3ank reaction solution and a 5.7 kbp fragment from a pET-MVHH reaction solution and purified by a purification kit (manufactured by Promega, trade name: Wizard SV Gel and PCR Clean-Up System). Subsequently, the aforementioned steps (4) to (8) are repeated.

(13) The sequence of the plasmid thus obtained is analyzed to confirm whether a desired DNA fragment (Sequence ID Nos. 15 and 16) is inserted or not. The plasmid obtained herein is designated as pET-scVA.

```
                                            Sequence ID No. 16
PWQVQLQESGPGLLKPSETLFLTCTVSGFSISGGYYWGWFRQPPG

KEREWIGSVYHSGSTYYNKSLESRVTISIHTSESQISLKLNSVTAADTAVY

SCARYRTAHPLWGQGTMVTVSSEFGGGGSGGGGSGGGGSNAADNTGTTPLH

LAAYSGHLEIVEVLLKHGADVDASDVFGYTPLHLAAYWGHLEIVEVLLKNG

ADVNAMDSDGMTPLHLAAKWGYLEIVEVLLKHGADVNAQDKFGKTAFDISI

DNGNEDLAEILQRL
```

Example 4

Expression of MBP-Bound VHH-Ankyrine Fusion Protein (1) Transformation

BL21(DE3) is transformed with the pET-scVA obtained in Example 3 by the heat shock transformation method employed in Example 3, spread on a LB/ampicillin agar plate, and allowed to stand still at 28° C. for 16 hours.

(2) Preliminary Culture

A colony is arbitrarily selected from those grown on the plate is arbitrarily selected and cultured in 3.0 mL LB/amp. medium at 28° C. overnight while shaking.

(3) Full-Scale Culture

The preliminary culture solution is poured in 750 mL of 2×YT medium and continued to culture at 28° C. At the time point when OD600 exceeds 0.8, IPTG is added up to a final concentration of 1 mM and culturing is continuously performed at 28° C. overnight.

(4) Purification (4-1) Acquisition of Cytoplasm Fraction

The resultant culture solution is centrifuged at 6000 rpm for 30 minutes at 4° C. and the culture supernatant is discarded to obtain a bacterial fraction. To the bacterial fraction, 15 mL of 20 mM Tris/500 mM NaCl (pH 7.9) (hereinafter referred to as "Tris solution") is added and allowed to sufficiently resuspend. The bacterial cells are broken by a French press to obtain a cytoplasm fraction as a solution containing broken cells.

(4-2) Metal Chelate Column

A desired protein is purified from the cytoplasm fraction by use of a His tag fused with the C terminal of the desired protein.

As a metal chelate column carrier, His-Bind (manufactured by Novagen) is used. Steps for preparing column, loading a sample, and washing are performed at 4° C. in accordance with the method recommended by the manufacturer. The desired protein, that is, His-tag fusion protein, is eluted by a 500 mM imidazole/Tris solution.

(4-3) Gel Chromatography

Purification is performed by gel filtration using Sephadex 75 (manufactured by Amersham Bioscience) in a buffer containing 50 mM Tris-HCl, 200 mM NaCl, 1 mM EDTA, pH 8, at a flow rate of 0.7 mL/min at 4° C. The peak suggesting a protein monomer of about 29 kDa is taken and subjected to the following evaluation analyses. The eluate solution is again dialyzed against a Tris solution used as an external solution to remove imidazole from the eluate solution. Subsequently, the external solution is replaced by a phosphate buffer (hereinafter referred to as PBS). In this way, buffer replacement is performed to obtain a solution for SPR evaluation.

Example 5

Preparation of MBP-Bound Ankyrine-Encoding DNA Fragment (2)

DNA of MBP-bound ankyrine is synthesized by an overlap PCR known in the art with reference to the sequences of DDBJ accession No. AY326424 (Sequence ID Nos. 5 and 6). The PCR is performed by using a pfu-turbo kit (manufactured by Stratagene) in accordance with the method recommended by the manufacturer. The obtained PCR fragment is designated ank2. A primer is designed so as to introduce restriction site NcoI at the 51 end and restriction site EcoRI at the 31 end of G3-ank (Sequence ID Nos. 9 and 10).

```
                                            Sequence ID No. 10
PLNAADNTGTTPLHLAAYSGHLEIVEVLLKHGADVDASDVFGYTP

LHLAAYWGHLEIVEVLLKNGADVNAMDSDGMTPLHLAAKWGYLEIVEVLLK

HGADVNAQDKFGKTAFDISIDNGNEDLAEILQRL
```

Example 6

Preparation of DNA Fragment of α-Helical Coiled Coil

DNA encoding a Jun protein Zipper sequence shown in Science, 1992, 254, 539-544 is prepared by an over-lap PCR. Restriction site EcoRI is inserted to the 5' end and restriction site HindIII at the 3' end of the synthetic DNA (Sequence ID Nos. 11 and 12) thus prepared. In the same manner, DNA encoding Fos protein shown in Cell, 1992, 68, 699-708 is synthesized. Restriction site EcoRI is inserted to the 5' end and restriction site HindIII to the 3' end of the prepared DNA (Sequence ID Nos. 13 and 14) thus prepared. The synthetic DNA fragments obtained above are designated as G3jun and G3fos, respectively.

```
                                           Sequence ID No. 12
EFGGGGSGGGGSGGGGSRIARLEEKVKTLKAQNSELASTANMLRE

QVAQLKQKVMNYRLC

Sequence ID No. 14
EFGGGGSGGGGSGGGGSLTDTLQAETDQLEDKKSALQTEIANLLK

EKEKLEFILAAYRLC
```

Example 7

Preparation of a Plasmid Expressing MBP-Bound VHH-Jun Fusion Protein

To pET-scVA obtained in Example 3, the PCR fragment obtained in Example 6 is inserted to prepare a plasmid expressing MBP-bound VHH-Jun fusion protein.

(1) The pET-scVA obtained in Example 3, and the DNA G3jun obtained in Example 6 are cleaved by restriction enzymes EcoRI and HindIII (both are manufactured by New England Biolabs) in the method recommended by the manufacturer and described in the technical bulletin.

(2) The resultant solution containing enzyme reaction products is subjected to agarose gel electrophoresis.

(3) An about 0.5 kbp fragment is cleaved out from a reaction product in a G3-jun reaction solution and a 5.7 kbp fragment from a pET-svVA reaction solution and purified by a purification kit (manufactured by Promega, trade name: Wizard SV Gel and PCR Clean-Up System).

(4) The DNA fragments obtained above are ligated with T4-Ligase (manufactured by Roche) for 2 hours in accordance with the method recommended by the manufacturer.

(5) JM109 competent cells (manufactured by Promega) are transformed by the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant solution and cultured at 37° C. for 1 hour while shaking. The obtained culture solution is centrifuged at 6000 rpm for 5 minutes and 700 µL of the supernatant is discarded.

(6) The remaining culture solution and the precipitate are stirred and spread on an LB/ampicillin (100 µg/mL) agar plate and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the obtained plasmid is analyzed and checked whether a desired DNA fragment (Sequence ID Nos. 17 and 18) is inserted or not. The plasmid obtained herein is designated as pET-VJ.

```
                                           Sequence ID No. 18
PWQVQLQESGPGLLKPSETLFLTCTVSGFSISGGYYWGWFRQPPG

KEREWIGSVYHSGSTYYNKSLESRVTISIHTSESQISLKLNSVTAADTAVY

SCARYRTAHPLWGQGTMVTVSSEFGGGGSGGGGSGGGGSRIARLEEKVKTL

KAQNSELASTANMLREQVAQLKQKVMNYFGC
```

Example 8

Preparation of a Plasmid Expressing Both MBP-Bound VHH-Jun Fusion Protein and MBP-Bound Ankyrine-Fos Fusion Protein A plasmid expressing MBP-bound ankyrine-Fos fusion protein is prepared by using the PCR fragments obtained in Examples 5 and 6. The vector used herein is pET-24d (manufactured by Novagen).

(1) Synthetic DNA ank2 obtained in Example 5 and pET-24d are cleaved by restriction enzymes NcoI and EcoRI (both are manufactured by New England Biolabs) in the method recommended by the manufacturer and described in the technical bulletin.

(2) The resultant solution containing enzyme reaction products is subjected to agarose gel electrophoresis.

(3) An about 0.6 kbp fragment is cleaved out from a reaction product in an ank2 reaction solution and a 5.3 kbp fragment from a pET-24d reaction solution and purified by a purification kit (manufactured by Promega, trade name: Wizard SV Gel and PCR Clean-Up System).

(4) The DNA fragments obtained above are ligated with T4-Ligase (manufactured by Roche) for 2 hours in accordance with the method recommended by the manufacturer.

(5) JM109 competent cells (manufactured by Promega) are transformed by use of the resultant ligation solution in accordance with a heat shock method (placed in ice, transferred to 42° C. for 90 sec, and transferred again into ice). After the heat shock treatment, 750 µL of LB medium (10 g of tryptone, 5 g of yeast extract, and 10 g sodium chloride/L) is added to the resultant solution and cultured at 37° C. for 1 hour while shaking. The obtained culture solution is centrifuged at 6000 rpm for 5 minutes and 700 µL of the supernatant is discarded.

(6) The remaining culture solution and the precipitate are stirred and spread on an LB/ampicillin (100 µg/mL) agar plate and allowed to stand still at 37° C. for 16 hours.

(7) The obtained colonies are cultured overnight in liquid LB medium containing ampicillin.

(8) From the bacterial cells obtained, the plasmid is recovered by using Minipreps SV plus DNA Purification system (manufactured by Promega) in accordance with the method recommended by the manufacturer.

(9) The sequence of the plasmid thus obtained is analyzed and checked whether a desired DNA fragment is inserted or not. The plasmid obtained herein is designated as pET-ank2.

(10) The obtained pET-ank2 and the DNA fragment G3fos obtained in Example 6 are digested with restriction enzymes EcoRI and HindIII (both manufactured by NEB) in accordance with the method recommended by the manufacturer.

(11) The resultant solution containing reaction products with enzymes is subjected to agarose gel electrophoresis.

(12) An about 0.5 kbp fragment is cleaved out from a reaction product in a G3-fos solution and a 5.9 kbp fragment from a pET-ank2 solution and purified by a purification kit (manufactured by Promega, trade name: Wizard SV Gel and PCR Clean-Up System). Subsequently, the aforementioned steps (4) to (8) are repeated.

(13) The sequence of the plasmid thus obtained is analyzed to confirm whether a desired DNA fragment (Sequence ID Nos. 19 and 20) is inserted or not.

```
                                          Sequence ID No. 20
    PWNAADNTGTTPLHLAAYSGHLEIVEVLLKHGADVDASDVFGYTP

LHLAAYWGHLEIVEVLLKNGADVNAMDSDGMTPLHLAAKWGYLEIVEVLLK

HGADVNAQDKFGKTAFDISIDNGNEDLAEILQEFGGGGSGGGGSGGGGSLT

DTLQAETDQLEDKKSALQC
```

The plasmid obtained herein is designated as pET-AF.

(14) PCR is performed using pET-AF as a template and primers AF-fw (Sequence ID No. 21) and AF-bk (Sequence ID No. 22) by a pfu-turbo kit (manufactured by Stratagene) in accordance with the method recommended by the manufacturer to obtain an about 0.9 kbp. fragment dna_af.

(15) The pET-VJ obtained in Example 7 and DNA fragment dna_af obtained in the step (14) are cleaved by restriction enzymes SphI and BghI (both are manufactured by New England Biolabs) in accordance with the method recommended by the manufacturer.

(16) The resultant enzyme reaction solution is subjected to agarose gel electrophoresis.

(17) An about 0.9 kbp fragment is cleaved out from a reaction product in a dna_af reaction solution and a 6.3 kbp fragment from a pET-VJ reaction product and purified by a purification kit (manufactured by Promega, trade name: Wizard SV Gel and PCR Clean-Up System). Subsequently, the aforementioned steps (4) to (8) are repeated.

(18) The sequence of the plasmid thus obtained is analyzed to confirm whether a desired DNA fragment is inserted or not. The plasmid simultaneously expressing both MBP-bound VHH-Jun fusion protein and MBP-bound ankyrine-Fos fusion protein is designated as pET-AFVJ.

Example 9

Expression of Both MBP-Bound VHH-Jun Fusion Protein and MBP-Bound Ankyrine-Fos Fusion Protein (1) Transformation BL21(DE3) is transformed with the pET-AFVJ obtained in Example 8 by the heat shock transformation method used in Example 3, spread on a LB/ampicillin agar plate, and allowed to stand still at 28° C. for 16 hours.

(2) Preliminary Culture

A colony is arbitrarily selected from those grown on the plate and cultured in 3.0 mL LB/amp. medium at 28° C. overnight while shaking.

(3) Full-Scale Culture

The preliminary culture solution are poured in 750 mL of 2×YT medium and continued to culture at 28° C. At the time point when OD600 exceeds 0.8, IPTG is added up to a final concentration of 1 mM and culturing is continuously performed at 28° C. overnight.

(4) Purification (4-1) Acquisition of Cytoplasm Fraction

The culture solution is centrifuged at 6000 rpm for 30 minutes at 4° C. and the culture supernatant is discarded to obtain a bacterial fraction. To the bacterial fraction, 15 mL of 20 mM Tris/500 mM NaCl (pH 7.9) (hereinafter referred to as "Tris solution") is added and allowed to sufficiently resuspend. The bacterial cells are broken by a French press to obtain a cytoplasm fraction as a solution containing broken cells.

(4-2) Metal Chelate Column

A desired protein is purified from the cytoplasm fraction by use of a His tag fused with the C terminal of the desired protein.

As a metal chelate column carrier, His-Bind (manufactured by Novagen) is used. Steps for preparing column, loading a sample, and washing are performed at 4° C. in accordance with the method recommended by the manufacturer. The desired protein, that is, His-tag fusion protein, is eluted by a 500 mM imidazole/Tris solution.

(4-3) Gel Chromatography

Purification is performed by gel filtration using Sephadex 75 (manufactured by Amersham Bioscience) in a buffer containing 50 mM Tris-HCl, 200 mM NaCl, 1 mM EDTA, pH 8.0 at a flow rate of 0.7 mL/min at 4° C. The peak suggesting a protein monomer of about 36 kDa is taken and subjected to the following evaluation analyses. The eluate solution is again dialyzed against a Tris solution used as an external solution to remove imidazole in the eluate solution. Subsequently, the external solution is replaced by a phosphate buffer (hereinafter referred to as PBS). In this way, buffer replacement is performed to obtain a solution for SPR evaluation.

Example 10

Evaluation of SPR

In comparison with the single stranded MBP-bound VHH/MBP-bound ankyrine fused protein obtained in Example 4, and the MBP-bound VHH-Jun/MBP-bound ankyrine Fos hetero dimer obtained in Example 9, the MBP bound antibody domain (VHH), which is a single domain protein bound to MBP and represented by Sequence ID No. 2 and the MBP-bound ankyrine represented by Sequence ID No. 6 were evaluated by SPR (manufactured by BIAcore). As a substrate, CM5 (manufactured by BIAcore) is used. MBP is immobilized onto the substrate in accordance with the method recommended by the manufacturer. The MBP immobilized chip thus obtained is subjected to evaluation under the conditions: running Buffer: 0.1% Tween 20/PBS, flow rate: 20 μL/min, and temperature: 25° C. As a result that a dissociation constant was evaluated by SPR, MBP-bound VHH shows $10^{-6}$M, MBP-bound ankyrine: $10^{-8}$M, single strand MBP-bound VHH/MBP-bound ankyrine fusion protein: $10^{-9}$M, and MBP-bound VHH-Jun/MBP-bound ankyrine-Fos: $10^{-9}$M. The capturing molecule according to the present invention has a high binding ability, compared to the capturing molecule known in the art binding to a target substance at a single epitope (or single site).

Example 11

Preparation of LSPR Sensor Element (1)

A sensor element is prepared by adding 200 μl of a gold colloidal solution (40 nmφ manufactured by Tanaka Kikinzoku) to the wells of a titer plate (manufactured by Sumitomo Bakelite Co., Ltd.) which is amino-treated and allowed to stand still at room temperature for 24 hours. Subsequently, the gold colloidal solution is removed from each of the wells, 200 μl of pure water is added and shaken for 10 minutes to remove the pure water added. This operation is repeatedly performed three times and thereafter dried by nitrogen gas. In this manner, it is confirmed that 20 to 25% of the bottom area of each well is covered by fine golden particles. Furthermore, the absorption spectrum obtained after 200 μl of the PBS solution is added to the wells of the sensor element of this Example has a peak at wavelength of near 510 nm.

Example 12

Preparation of LSPR Detection Sensor Element (1)

To impart a target substance capturing ability to the sensor element prepared in Example 11, the protein obtained in Example 9 is used as a target substance capturing material. A method of immobilizing the protein onto the surface of a golden construct will be explained below.

First, 0.05% Tween 20/PBS solution is prepared so as to contain the protein obtained in Example 9 having a thiol group having a high affinity for gold which a material for forming the construct of this Example at the carboxyl terminal in an amount of 1 μM. The protein solution thus obtained is dispensed to the wells of the detection element obtained in Example 11 in an amount of 200 μl per well. After the wells are allowed to stand still at room temperature for 2 hours, the solution is removed from the wells. Subsequently, 200 μL of the 0.05% Tween 20/PBS solution is added to each well. After the wells are shaken for 10 minutes, the 0.05% Tween20/PBS solution added above is removed. This operation is repeatedly performed three times. By virtue of this operation, the peak of the absorption spectrum obtained after 200 μL of the PBS solution is added to the wells of the detection element shifts toward near a wavelength of 530 nm.

The concentration of MBP in a specimen can be specifically determined by use of the detection element obtained in this Example in accordance with the following operation.

To each of the wells of the detection element of this Example, a specimen containing a target substance MBP is added and allowed to stand still for 2 hours. In this way, MBP is captured by the wells. After the specimen is removed from each of the wells, 200 μL of a 0.05% Tween 20/PBS solution is added to each well and shaken for 5 minutes and then the 0.05% Tween 20/PBS solution added above is removed. This operation is repeatedly performed three times. Furthermore, the same operation is repeated three times by replacing the solution with a PBS solution to wash the wells.

Finally, a PBS solution is added to the wells and the absorption spectrum is obtained. When the absorption spectra are compared before and after the reaction, it is observed that the peak shifts when a target substance is bound to the surface of the detection element by a specific antigen-antibody reaction. The intensity of the peak of the absorption spectrum or the correlation between the shift amount of the peak wavelength and the MBP concentration has been obtained by use of a MBP control solution known in concentration. Therefore, the MBP concentration of the specimen can be obtained even if it is small.

Example 13

Preparation of a Plasmid Expressing Both MBP-Bound VHH-Jun Fusion Protein and MBP-Bound Peptide-Fos Fusion Protein A plasmid expressing both MBP-bound VHH-Jun fusion protein and MBP-bound peptide-Fos fusion protein is prepared in substantially the same manner as in Example 8, except that the ankyrine encoding base sequence of the pET-AFVJ plasmid prepared in Example 8 is replaced by a base sequence encoding the MBP-bound peptide represented by Sequence ID No. 24: TPIHRRRQFNTG (base sequence represented by Sequence ID No. 23). The obtained plasmid is designated as pET-PFVJ.

Example 14

Expression of MBP-Bound VHH-Jun Fusion Protein and MBP-Bound Peptide-Fos Fusion Protein MBP-bound VHH-Jun fusion protein and MBP-bound ankyrine-Fos fusion protein are obtained in the same manner as in Example 9, except that the protein expressing plasmid pET-AFVJ is replaced by the protein expressing plasmid pET-PFVJ obtained in Example 13.

Example 15

Evaluation of SPR (2)

MBP-bound VHH-Jun fusion protein and MBP-bound peptide-Fos fusion protein hetero dimer obtained in Example 14 was evaluated for SPR (manufactured by BIAcore) in the same manner as in Example 10. As a result that a dissociation constant was evaluated by SPR, MBP-bound VHH-Jun/MBP-bound peptide-Fos showed $10^{-8}$ M. From this, it is demonstrated that the capturing molecule according to the present invention has a high binding ability compared to the capturing molecule known in the art binding to a target substance at a single epitope (or a single site).

Example 16

Preparation of LSPR Sensor Element (2)

Figure 2:
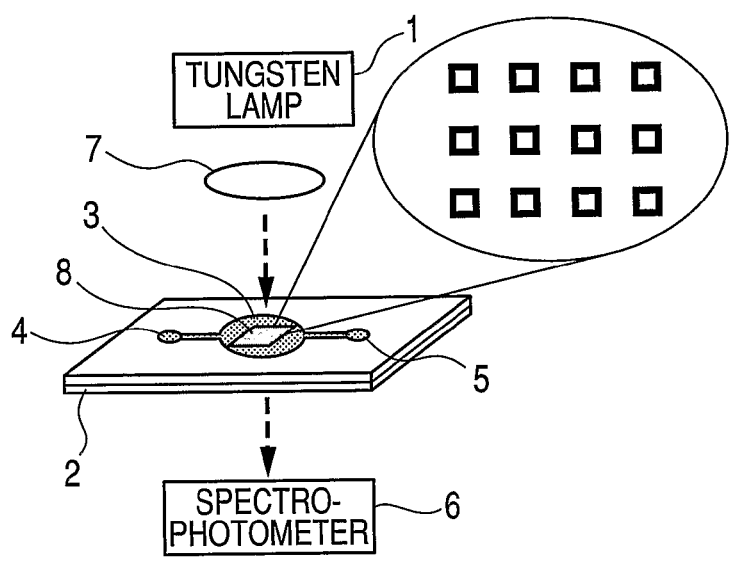
FIG. 2 is a schematic view of a detection apparatus used in Examples 17 and 18.
Figure 3:
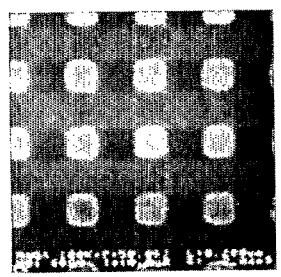
FIG. 3 is a SEM photograph of a sensor element according to Example 17.

FIG. 2 shows a schematic structure of the detection apparatus used in this Example. Light from tungsten lamp 1 is collimated by a collimator lense 7. Absorption spectrum of transmitted light through element 8 is obtained by spectrophotometer 6. Reference numeral numbers 2, 3, 4 and 5 indicate substrate, reaction well, inlet and outlet respectively. A detection element 8 was prepared by forming a thin golden film of 20 nm thick on a quartz substrate of 625 μm thick and patterning the film into a predetermined pattern by an electron beam lithography apparatus. As shown in SEM (scanning electron microscopic) photograph of FIG. 3, the outer shape of the planar metal construct is a regular square of 200 nm×200 nm. The shape of the internal opening portion is not always formed in the same as that of the outer shape depending upon the high or low resolution. In the pattern, metal constructs are arranged in the form of array at the intervals of 250 nm in the area of 3 mm×3 mm. The absorption spectrum of the construct has a peak near a wavelength of 800 nm.

Example 17

Preparation of LSPR Detection Element (2)

Next, the capturing molecule according to Example 9 is immobilized onto the surface of the metal construct in the same manner as in Example 12. A method for immobilizing the capturing molecule onto the surface of a golden construct will be described below.

First, 0.05% Tween 20/PBS solution is prepared so as to contain the protein obtained in Example 9 having a thiol group having a high affinity for gold which is a material forming the construct of Example 16 at the carboxyl terminal in an amount of 1 µM. The protein solution thus obtained is dispensed to the array of the detection element obtained in Example 16 in an amount of 200 µl per array. After the array is allowed to stand still at room temperature for 2 hours, the solution is removed from the array. Subsequently, 200 µL of the 0.05% Tween 20/PBS solution is added to the array. After the array is shaken for 10 minutes, the 0.05% Tween 20/PBS solution added above is removed. This operation is repeatedly performed three times. By virtue of this operation, the surface of the construct is modified by the capturing molecule of Example 9.

Example 18

Evaluation of LSPR (2)

The concentration of MBP contained in a specimen can be specifically determined by the operation below.

(1) A specimen containing a target substance MBP is fed into the element manufactured above through an inlet 4 and MBP is captured by the construct.

(2) The specimen is discharged and a phosphate buffer is fed through the inlet 4 to wash the interior of a reaction well 3.

(3) Finally, the phosphate buffer is loaded and the absorption spectrum of the golden construct is obtained.

The absorption spectra are compared before and after the reaction. When a target substance is bound to the surface of the detection element by a specific antigen-antibody reaction, the peak of the absorption spectrum shifts. The intensity of the peak of the absorption spectrum or the correlation between the shift amount of the peak wavelength and the MBP concentration has been obtained by use of a MBP control solution known in concentration. Therefore, the MBP concentration of the specimen can be obtained even if it is small.

This application claims priority from Japanese Patent Application No. 2005-160737 filed May 31, 2005, which is hereby incorporated by reference herein.

The invention claimed is:

1. A capturing molecule having not less than two domains specifically binding to different sites of a target substance, wherein the not less than two domains comprise
   (1) a first domain having a hypervariable loop structure at a binding site to the target substance, and
   (2) a second domain having no hypervariable loop structure at a binding site to the target substance.

2. The capturing molecule according to claim 1, wherein the first domain has at least one variable region of an antibody against a first epitope of the target substance.

3. The capturing molecule according to claim 1, wherein the first domain has a hypervariable loop structure of an antibody against a first epitope of the target substance or not less than one loop structure comprising part of the hypervariable loop structure.

4. The capturing molecule according to claim 2, wherein the first domain is a camel heavy-chain antibody variable region.

5. The capturing molecule according to claim 1, wherein the binding site of the second domain binding a second epitope of the target substance is an exterior surface of a polypeptide chain which forms a secondary structure.

6. The capturing molecule according to claim 5, wherein the secondary structure comprises an a-helix structure.

7. The capturing molecule according to claim 5, wherein the binding site of the second domain has at least comprising a basic structure repeat of a secondary structure of a polypeptide chain.

8. The capturing molecule according to claim 1, wherein the not less than two domains are arranged on a same polypeptide.

9. The capturing molecule according to claim 1, wherein the not less than two domains are arranged on different polypeptide chains respectively, and at least a portion of each of the polypeptide chains are associated to form a domain complex.

10. A method of detecting a target substance comprising the steps of
   reacting the capturing molecule according to claim 1 with a specimen, and
   detecting binding of the target substance and the capturing molecule when the specimen contains the target substance.

11. An apparatus for detecting a target substance comprising
   the capturing molecule binding to a target substance according to claim 1,
   a detecting element having the capturing molecule on at least one portion of a surface thereof,
   holding means for holding the element, and
   detecting means for detecting the target substance by the element.

12. A kit for detecting a target substance comprising
   the capturing molecule according to claim 1, and
   a reagent for detecting the binding of the capturing molecule and the target substance.

* * * * *